United States Patent [19]

Pleass et al.

[11] Patent Number: 5,108,907
[45] Date of Patent: Apr. 28, 1992

[54] LASER DOPPLFER SPECTROMETER FOR THE STATISTICAL STUDY OF THE BEHAVIOR OF MICROSCOPIC ORGANISMS

[75] Inventors: C. M. Pleass, Havre de Grace, Md.; Dean Dey, Lewes, Del.

[73] Assignee: University of Delaware, Newark, Del.

[21] Appl. No.: 651,402

[22] Filed: Sep. 17, 1984

[51] Int. Cl.$^5$ .......................... C12Q 1/04; C12Q 1/02; C12Q 1/22; G01P 3/36

[52] U.S. Cl. ........................................ 435/34; 435/29; 435/31; 435/32; 435/173; 356/28.5

[58] Field of Search .................... 435/29, 30, 34, 173; 356/28.5

[56] References Cited

U.S. PATENT DOCUMENTS 4,061,543 12/1977 Bean et al. ............................ 435/32
4,577,963 3/1986 Traina ................................. 356/28.5

OTHER PUBLICATIONS

Koyama et al., Experientia, vol. 35, Jan. 15, 1979, pp. 65-67.
Ross et al., "The Measurement of Sperm Motility Using the Fibre Optic Dopper Anemometer, FODA" In: Biomedical Applications of Laser Light Scattering, Sattele et al., (ed.) Elsevier Biomedical Press, 1982, pp. 239-248.
Johnson, "A Laser-Doppler Microscope for Biological Studies", In: Biomedical Press, 1982, pp. 239-248.
Johnson, "A Laser-Doppler Microscope for Biological Studies", In: Biomedical Applications of Laser Light Scattering, Sattelle et al. (ed.) Elsevier Biomedical Press, 1982, pp. 391-402.
Mishina et al., Applied Physics, vol. 5, (1975), pp. 351-359.
Mishina et al., Applied Optics, vol. 14, No. 10, Oct. 1975, pp. 2326-2327.
Herbert et al., Applied Optics, vol. 18, No. 5, Mar. 1979, pp. 588-590.
Lee, "Applications of Laser Light Scattering in Fertility Study" In:Biomedical Applications of Laser Light Scattering, Sattelle et al. (ed.), Elsevier Biomedical Press, 1982, pp. 209-219.
Jouannet, "Measurement of Human Sperm Motility Based on an Optical Doppler Effect", In:Spermatozoon, Faucett et al. (ed.), Urban & Schwarzenberg, Baltimore, 1979, pp. 427-430.
Nultsch, "Movements", In:Algal Physiology and Biochemistry, Stewart (ed.), vol. 10, University of California Press, Berkely, 1974, pp. 864-893.
Koyama et al., Experientia, vol. 31, No. 12, Dec. 15, 1975, pp. 1420-1422.

Primary Examiner—Christine Nucker
Assistant Examiner—David R. Preston
Attorney, Agent, or Firm—Connolly & Hutz

[57] ABSTRACT

A differential laser doppler biospectrometer for monitoring microbiota movement in a medium, which, preferably is quiescent. One of the laser beams is shifted in frequency to enable monitoring of small movement data velocity and/or direction). Average size of individuals and growth rate of the total number of organisms in suspension can be obtained. Exogenous stimuli, such as electric and magnetic fields, trace chemical additions or EM radiation are provided at selected times in the natural rhythm circadian cycle of the microbiota, and several such stimuli can be applied simultaneously. The measurement system is so sensitive that it can detect movement changes due to very weak energy stimuli transmitted to microbiota free to move in an established zone. In addition, holographic recordings of the microbiota can be made.

9 Claims, 21 Drawing Sheets

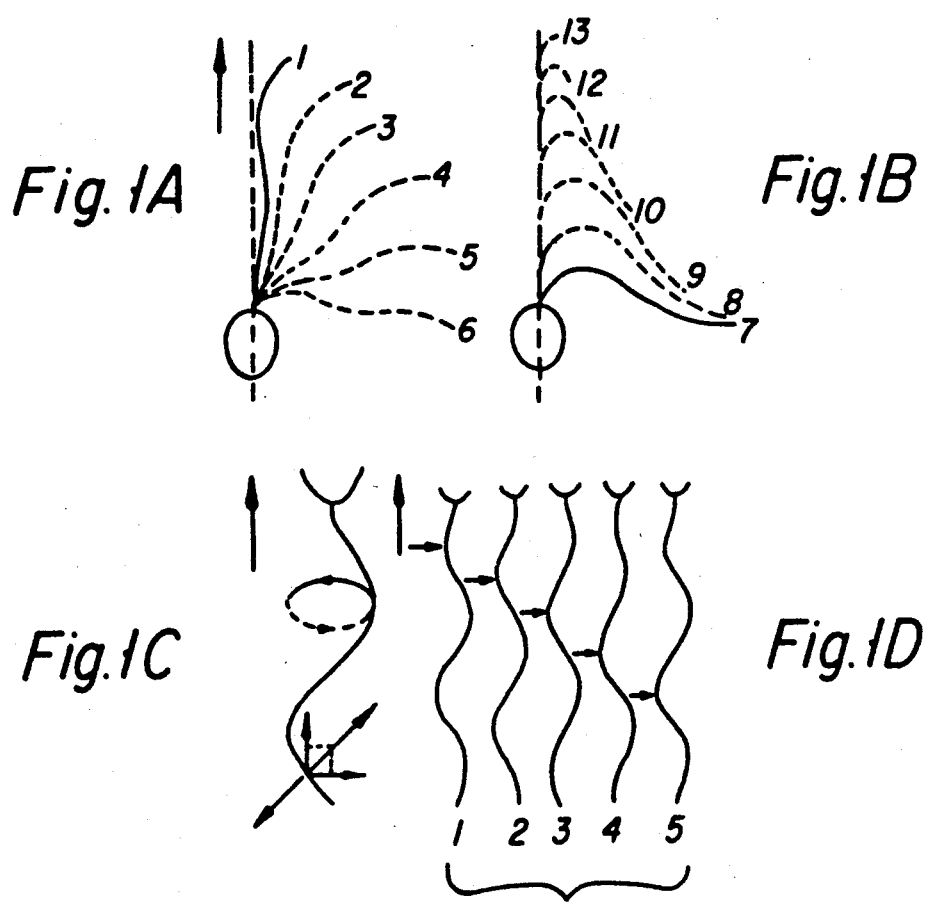
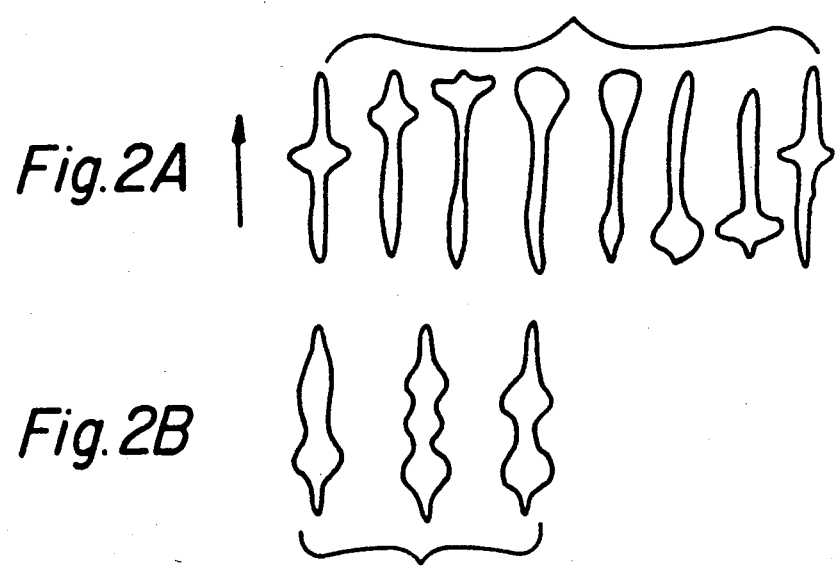
Fig.1A Fig.1B Fig.1C Fig.1D
Fig.2A Fig.2B

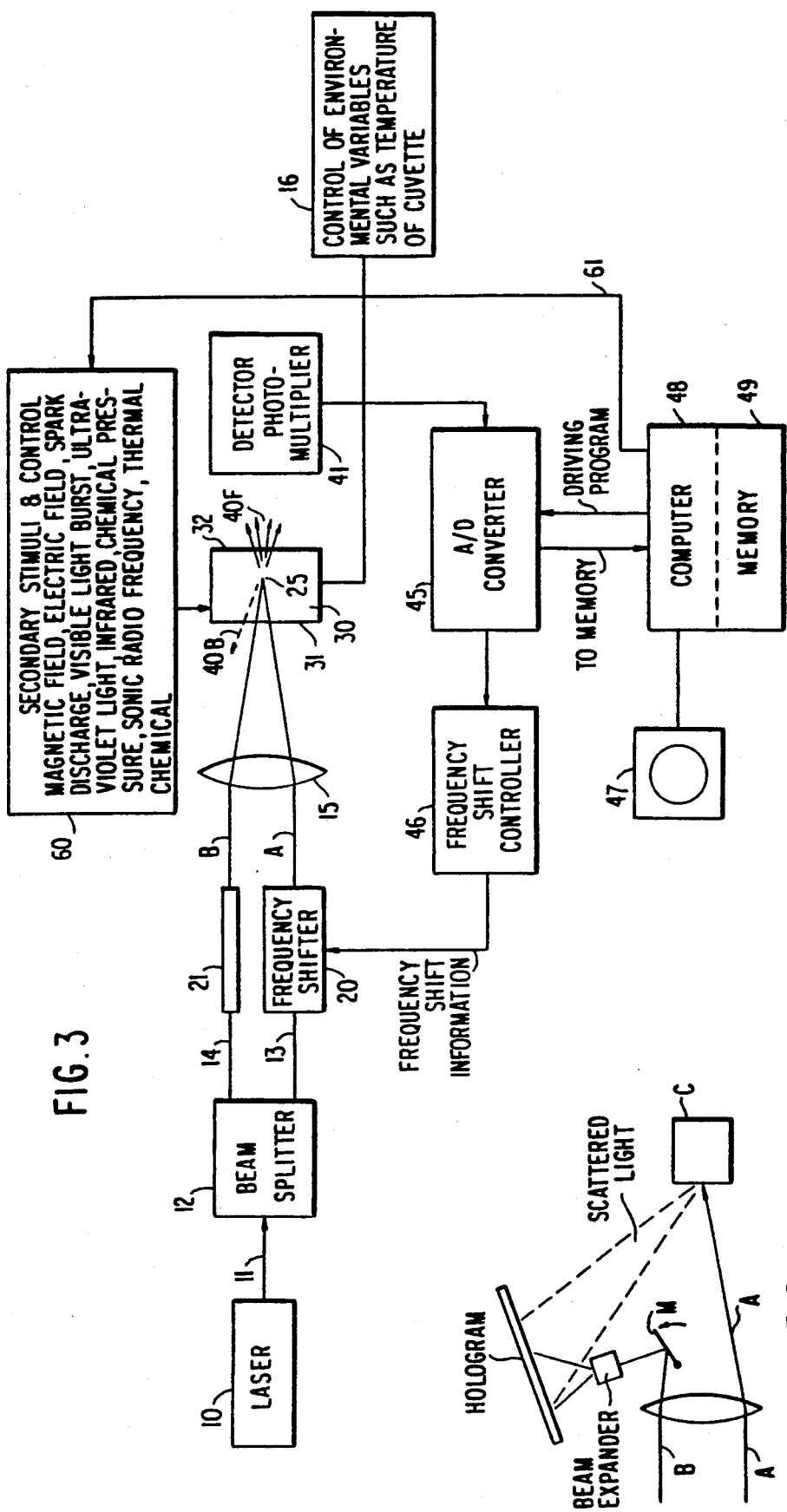

LASER DOPPLER SPECTROMETER FOR THE STATISTICAL STUDY OF THE BEHAVIOR OF MICROSCOPIC ORGANISMS

BACKGROUND AND BRIEF DESCRIPTION OF THE INVENTION

Differential Laser Doppler (DLD) is a technique well known to physicists interested in fluid flow and microturbulence. Microscopic particles in moving fluids can scatter coherent laser light and the Doppler frequency shift provides a very accurate measure of fluid velocity.

A primary objective of this invention is to provide an improved apparatus for tracking, monitoring and identifying microbiota swimming in a medium, which is preferably quiescent, and to provide a sensitive method for rapidly measuring very small changes in their motility and direction of movement. Other parameters such as the average size of the individuals, and the growth of the total number of organisms in suspension can also be monitored. The present invention can readily be applied to phytoplankton, zooplankton, bacteria, or miniature ecosystems containing a variety of suspended microscopic plants and animals. The invention is useful in studies in areas of ecology, medicine, cell biology, etc.

A number of articles of interest are in a text entitled "The Application of Laser Light Scattering to the Study of Biological Motion" edited by J. C. Ernshaw and M. W. Steer, copyright 1980, Plenum Publishing Corp. Several articles in this text deal with laser light measurements of motility of living cells and microorganisms, with particular reference being made to the article by J. C. Ernshaw entitled "Laser Doppler Velocimetry" which describes a differential laser doppler in which one of the beams was electronically down mixed to give effective frequency shifts as low as 10 kHz, and the article by J. P. Boon entitled "Motility of Living Cells and Microorganisms" which describes the effect of stimuli on the motility of cells.

The use of a frequency shifter in studies of reversing flows, high turbulance and fluctuating flows with zero mean velocity enables the determination of direction and magnitude of flow. Frequency shift also allows optimum matching of the doppler signal to the range of the frequency tracker.

Commercial frequency shifters, such as DISA frequency Shifter Model 55N10 allows up to 54 settings ($\pm 9$ mHz) to help optimize the signal. However, as indicated above, the lowest shift available is 10 kHz. It is an important objective of this invention to accurately identify and define doppler frequencies corresponding to the swimming velocities of microbiota and these are commonly found to be less than $20 \times 10^{-6}$ msec$^{-1}$ (see Table 1, W. Nultsch "Movements in Biochemistry and Physiology of Algae", 1974, pg. 865), corresponding to doppler frequencies substantially less than 1 kHz.

According to the present invention, the shift is related to the motility range of the microorganisms. Thus, the frequency shifter according to the present invention is at a value of about 5.5 kHz. This provides velocity resolution at magnitudes $<20 \times 10^{-6}$ msec$^{-1}$, ten times better than Ernshaw et al. (e.g. $+0.3$ msec$^{-1}$). This enhanced resolution is critical for studies of microorganisms where subtle changes in velocities in the order of $1 \times 10^{-1}$ msec$^{-}$ can be caused by various applied stimuli. The earlier frequency shift to 5.5 kHz is not absolute, and shift ranges for specific biota are intended to be encompassed in this invention. Thus, an important feature of the invention is in the use of a multi-beam differential laser doppler system in which the frequency shift of one of the beams relative to the others is very low, in this preferred embodiment circa 5.5 kHz. Another feature of the invention is that specific frequency shifts are related to the motility characteristics of specific microbiota. In the most complete manifestation of this invention, apparatus to analyze frequencies below 10 kHz is included together with optional shifts appropriate to that very low range.

The invention has particular advantage and usefulness when used to describe the effects of exogenous stimuli. Electric fields, magnetic fields, and e.m. radiation can be applied to the sample volume without interrupting the analysis. Data already accumulated shows dramatic and previously unrecognized effects upon application of external fields to seawater suspensions of single celled marine algae and shellfish sperm.

The measurement format bears some resemblance to spectrophotometry; the same (static or flow) cell with transparent input and exit ports admits split laser beams which cross within the sample volume to form virtual fringes. Scattered light from microbiota crossing those fringes is picked up by a photomultiplier and processed electronically to provide an input to a computer data file. When interrogated this file yields histograms, x-y plots of individual algal velocities or group statistics, and spectra which report the various motions perceived by the laser light including translational and rotational modes. Velocities reported may span the range from 10 to less than $10^{-6}$ msec, allowing the characterization of the complete body kinetics of a culture of micro organisms. Unattended operation over many reproductive cycles has been demonstrated, and if provision is made to sustain a community of microbiota, it can be followed indefinitely.

Most importantly, coincidental stimuli can be studied at known points in the circadian cycle or some other temporal natural rhythm. The system can continuously track the diurnal or circadian rhythm. A 48 hour run would result in ca. $10^6$ data points defining the behavior of five to ten generations. One such run with the algae Tetraselmis is illustrated in FIG. 5. In the run each printed point was an average over a one (1) second interval. Each one second average was derived from circa 5 individual measurements. According to the invention, computer programs can impose fields and/or radiation at chosen intervals during the ongoing "baseline" run. Already data is available which dramatically illustrate the transient effect of a nearby spark discharge on Tetraselmis, and its subsequent rapid adaptation. Response appears to vary markedly with the phase of the circadian cycle. Similar observations have been made for the dinoflagellate Gyrodinium. Magnetic fields also cause dramatic changes in vector and velocity in some species. Coincident stimuli and the phase of the circadian cycle are likely to dominate biological response, just as they do in Homo sapiens. Thus, if an individual responds to a sound which they have never heard before, their nervous system response is likely to be quite different depending on the state of the other system variables. Is it a sunny noontime or a dark cold winter night? Quite different biological changes may result depending on these and other more subtle coincidental stimuli. Generally, the biological effects will be transient, but in extreme cases they may be permanent.

The rapidity with which the invention's data collection proceeds makes wide band frequency scanning practical within a small increment of circadian phase angle.

The shift at 5.5 kHz does not improve the accuracy of the instrument per se. The 5.5 kHz shift does recognize that most of the swimming velocities (i.e. time for algae to get from A to B, as distinct from the substantial velocity of his flagellum, or its wobble), for minute organisms are found at the very low end of the 1-10 kHz range, and allows the signal to be electronically shifted towards the center of its range, which, according to this invention, allows laser doppler its best chance to perform. The accuracy of the present instrument still does not exceed plus or minus about 0.5% of the range maximum in the 8-bit mode, for individual measurements. The instrument may be further adapted to break the low range down into smaller pieces corresponding to the transmission of a larger number of bits of information. There is no technical obstacle here and in fact, this merely involves selecting the proper frequency counter. Utimately, the accuracy to which you can measure individual velocities is limited by the frequency counting mechanism (which can be so accurate that it is not a significant limitation) and by the trade-off between the number of bytes used to transmit the number and the corresponding transmission time. In prior art work, there was little interest in individual partical velocities. Investigators using LDV (laser doppler velocimeter) have been concerned with average velocities. The prior art was not concerned with the unique problem of tracking individuals accurately. Average velocity and overall direction on flow were the parameters from which they deduced their results. The larger the block used for averaging the less one is able to distinguish by/or multi-modality in a spectrum.

The data obtained using this invention is good to $10.3 \times 10^{-6}$ msec$^{-1}$. Because each point represents the average over the smallest integration interval available in the Disa instrument-one second. Depending on the algal concentration, circa 10 individual values will have been accumulated in the one second "stack" inside the integrator before the average is set out. Because averaging prior to transmission reduces the load on the transmission line Disa can afford to handle all this data in a 16-byte mode.

The limit improved by the accuracy of the voltage controlled (phase lock) oscillator which is the key element in the frequency monitoring circuit, sets up with a demonstrable accuracy of $10.3 \times 10^{-6}$ msec$^{-1}$ for one second averages. The instrument can be modified to improve the accuracy of frequency measurement in the 1-10 kHz range. For example, a Hewlett Packard frequency counter with 12-byte output would break the 1-10 kHz range into $2+2^2+2^3+2^4+2^5+2^6+2^7+2^8+2^9+2^{10}+2^{11}+2^{12}$ (e.g. about 4096 parts), which is all the accuracy one would ever ask for at the low velocities of interest.

A major aspect of the invention is the recognition that modified laser doppler permits very accurate measurement of individual motions (including flagella, whip, wobble, etc.) at very high data rates, allowing these data to be processed statistically to give higher significant measures of:

1) Temporal changes (such as rhythm, diur changes in direction and velocities).

2) The effects of exogenous stimuli including traces of foreign materials of importance in pollution ecology.

3) Identification of a species.

Possible modifications of reproductive behavior must be studied within an experimental framework which permits control of coincidental stimuli and circadian phase angle. Such effects could be beautifully explicit according to this invention using sample numbers in the $10^{-4}$ to $10^{-6}$ range.

In summary, the present invention can rapidly describe:

1. Frequency response,
2. Frequency/intensity relationships, and
3. The effect of coincidental stimuli and the variation of the effect with circadian phase angle.

These descriptions can be applied to:

1. Motility,
2. Individual growth rate,
3. Reproduction, and
4. Aging.

As noted earlier, the invention contemplates a wide range of exogenous stimuli and can be one or more stimuli, applied at a selected phase or time in the natural rhythm of the microbiota, selected from the following:

a) a magnetic field,
b) an electric field,
c) complex fields as from a spark discharge,
d) visible intensity/wavelength light in the visible spectrum,
e) x-rays,
f) ultraviolet light,
g) infrared light,
h) chemical,
i) pressure,
j) sonic,
k) radio frequency,
l) thermal.

It is well accepted that the motility of a plankton population is one good measure of its vigor and good health. The invention is valuable as a method of studying positive and negative exogenous effects on the mass of microbiota which occupy the most influential position at the base of the food web. Thus an important aspect of the invention is the use of differential laser Doppler in a biospectrometer, within which motility, reproduction and growth can be monitored at known circadian phase angles, in the presence of chosen exogenous stimuli such as electric and magnetic fields, trace chemical additions, or em radiation.

In the biospectrometric mode, far more than simple swimming velocity is detected using the invention. In fact, maximum sampling rate increases in proportion to velocity (because it takes less time to analyze enough virtual fringes to characterise the velocity to a given accuracy). The peaks on FIG. 7e for example, are identified by sampling rate 1 to show how easy it is to characterise the higher velocities/frequencies. It is believed that these high frequency motions will tend to be the most sensitive to exogenous stimuli.

BRIEF DESCRIPTION OF THE DRAWINGS

The invention will be described in greater detail in the following specification in conjunction with the accompanying drawings wherein:

FIGS. 1a-1c, illustrate patterns of flaggellar movement in algae microbiota which can be monitored by this invention, FIGS. 2a-2b, illustrate patterns of metabolic movements another form of microbiota which can be monitored by the invention, FIG. 3 is a schematic block diagram of an apparatus incorporating the invention, FIG. 4 is a schematic diagram of a modification of the invention for holographic monitoring of microbiota, FIGS. 6a through FIG. 6l, are histograms of various microbiota illustrating the wide range of application of the invention to monitoring microbiota.

DETAILED DESCRIPTION OF THE INVENTION

Figure 6D:
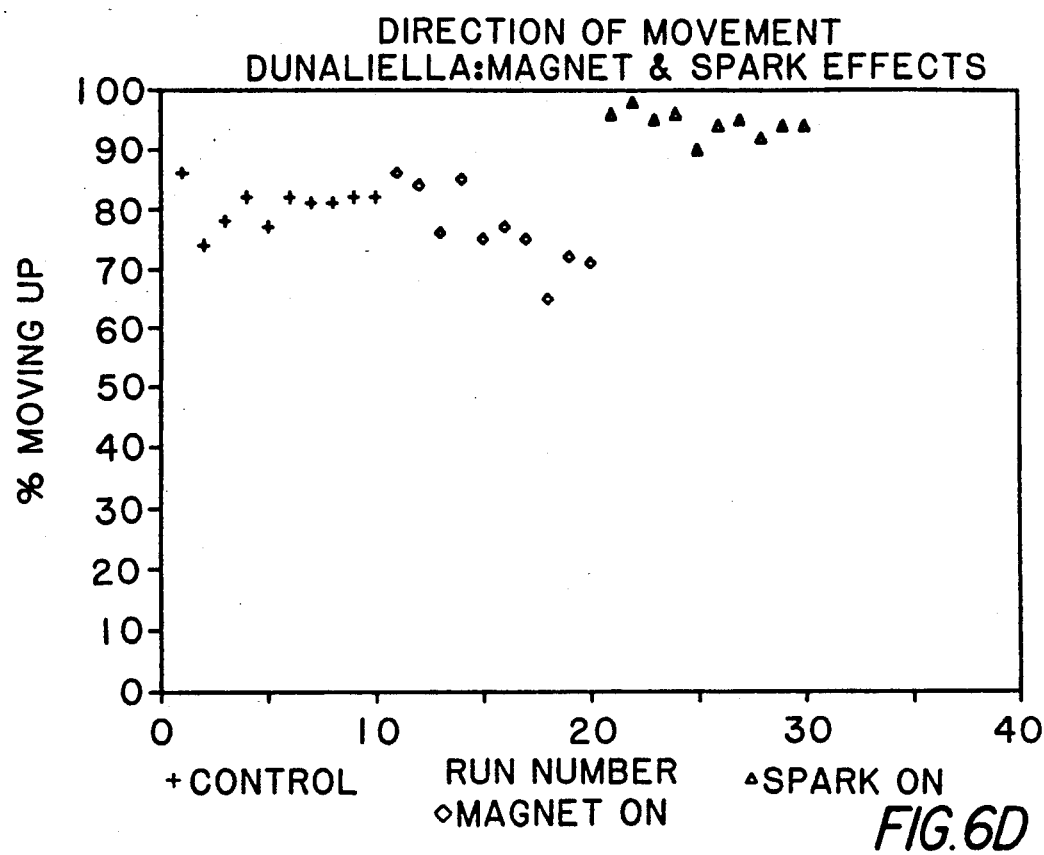
Figure 6E:
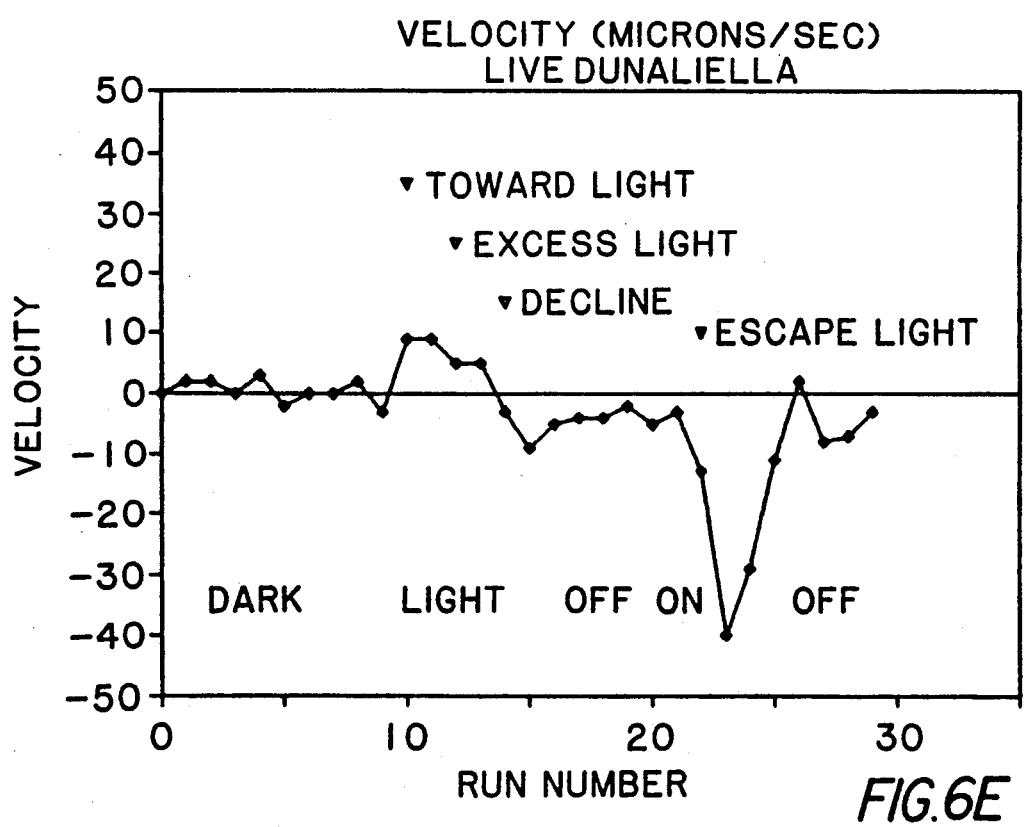
Figure 6F:
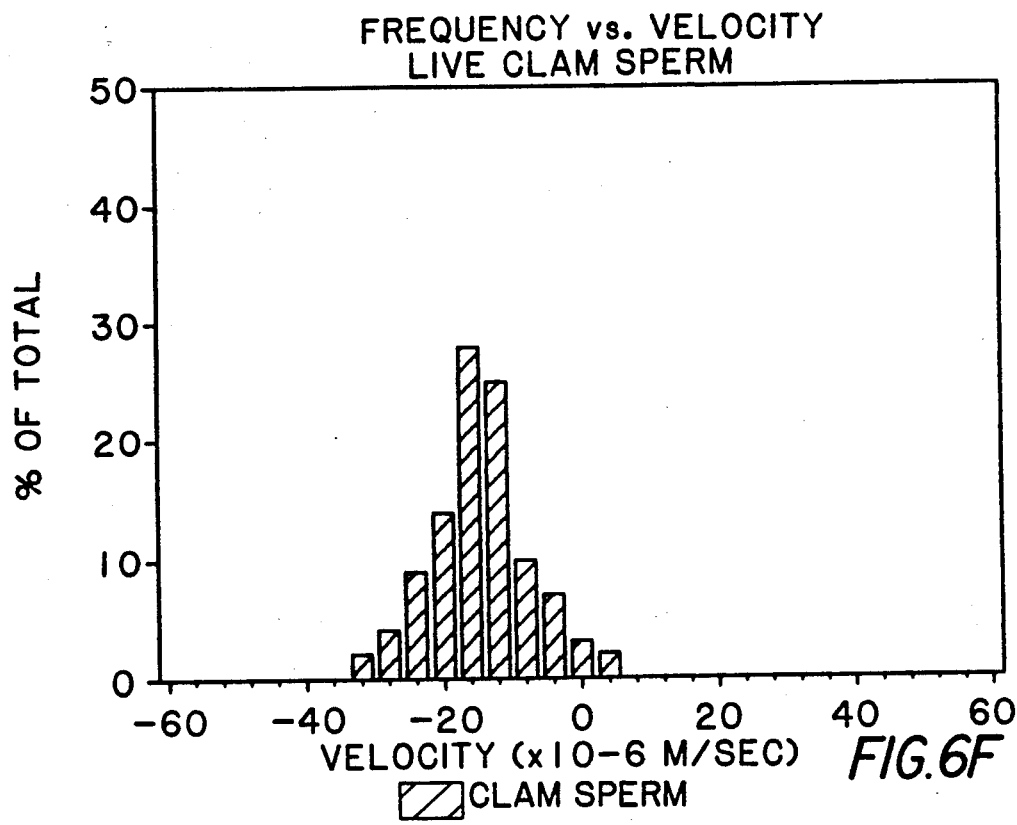
Figure 6G:
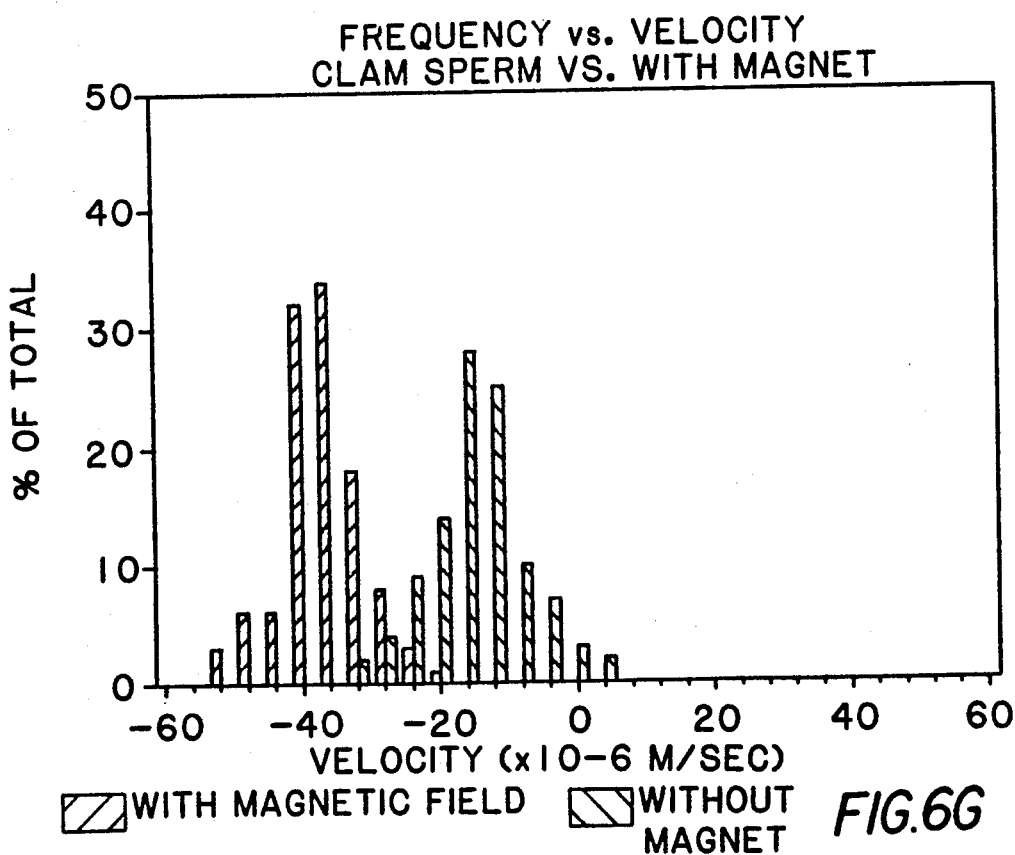

FIGS. 1a-1c show patterns of flagellar movement of algae, FIG. 1a showing "pull" type with FIG. 1Aa showing the power stroke and FIG. 1Ab showing the return strike; FIG. 1b shows "propeller" type locomotion and FIG. 1c showing "undulatory" type motion, with a wave (arrow) running over the flagellum. Successive positions are numbered. In FIGS. 2a and 2b, metabolic movements of the microbiota euglena deses is shown. FIGS. 2a1-8 showing a single wave running over the cell in the direction of the arrow and FIG. 2b1-3 shows two or three waves running simultaneously. These diagramatic sketches are from the text "Algal Physiology and Biochemistry" University of California Press, 1974, Chapter 31 by W. Nultsch entitled "Movements". These forms of motion can be used to detect the species.

In the schematic block diagram of FIG. 3, a laser 10 issues a beam 11 of laser light (at about 6348-A) from a gas laser to a beam splitter 12, producing at least a pair of beams 13 and 14 which are transmitted along separate paths A and B to lens 15. Beam 13 is passed through optical frequency shifter 20 which is a Bragg cell, and beam 14 is passed through a compensatory glass rod 21. Both beams are converged to a cross-over point 25 by lens 15. It will be appreciated that the beams can be generated by solid state lasers and carried by fiber optics to the cross over point 25.

A sample holder 30, which is a conventional cuvette having a pair of windows 31, 32 for permitting light to pass and which may include conventional water jacket for temperature control (not shown), controlled by environmental control 16 etc. Sample holder 30 is positioned so that the cross-over zone or area of the two laser beams 13 and 14 is within the volume of fluid carried in the cuvette 30.

In a differential laser doppler, the two beams 13 and 14 are of approximately equal intensity and superposition of the two beams forms virtual fringe patterns of planes having a strong electromagnetic field separated by planes having weak electromagnetic field. A microbiota, having the motion patterns illustrated in FIGS. 1a-1c swimming across the fringe pattern with a velocity component perpendicular to the fringe planes will scatter light at a frequencies related to its various motions. Such scattered light 40F and 40B is detected by a photomultiplier 41. It will be appreciated that photomultiplier 41 can be located to detect back scattered light 40B or forward scattered light 40F. Photomultiplier 41 converts or transduces the scattered light 40 to an analog signal which can be recorded. In the present case, the electrical analog signal is applied to an analog to digital converter 45 and to a frequency shift controller 46. Digital signals from converter 45 are applied to a display 47 which may be an oscilloscope, a computer 48 and a memory 49 which can be magnetic disk or tape.

While CW lasers are preferred, pulsed lasers can also be used in the practice of the invention. While reference herein has been made to gas lasers, it is within the scope of this invention to use solid state components. Thus, a Gallium Arsinide solid state laser with a fiber optic coupling element defining the paths for laser light through the frequency shifter to the detection zone of the sample can be used in the practice of the invention. The most desirable manifestation of the differential laser doppler apparatus would be one in which four laser beams converged on the measuring volume, to give very precise information on the vector of each microbiota whose size and velocity was examined.

As noted above, the differential laser doppler including frequency shift means 46 and control circuitry therefor is conventional and reference is made to the Instruction Manual published by DISA Information Department entitled "DISA 55X Modular LDA Optics" for all laser components and detector devices or components referred to herein and the Instruction Manual published by the same entity entitled "DISA 55N10 LDA Frequency Shifter" for details of frequency shift techniques utilized in this invention.

One general type of program used in this invention is illustrated by the laser 16 program. This program is used to interface the Tecmar, Inc. IEEE 488 board to the computer (an IEEE 488 board is an industry communications standard by which different instruments can send and receive data).

In this program example, lines 10-130 collects the initial information and sets up the interface board. Lines 150-200 sets the Tracker internal switches. Lines 210-270 collects data from the Tracker, and the lines 280-360 calculates the velocity and displays it. Lines 361-450 collects the data, calculates various statistics and prints the results of the calculations. Lines 470-610 stores the data and data summary on a floppy disk. The remaining program executes the commands and runs the Tecmar, Inc. board. In practice, large sections of the Tecmar program are not used and must be used for research purposes. It allows the rapid collection of large bodies of data, and the storage of these data. In addition, these data are accurate to 0.3 microns per second and can be presently collected continuously at 6-8 measurements per second.

There are often beat frequencies which correspond to the motion of flagella or cilia or the means of propulsion (shown in FIGS. 1a-1c and 2a and 2b) used by the organism which can either be ignored in favor of a study of the overall motion, or, if desired, separated analytically from the former so that the effects of exogenous stimuli on them can be examined. Normally, flagella or cilia would beat rhythmically to induce motion. In distressed microbiota (animal or plant) the movements may become erratic.

Laser 16

10 REM laser 16. bas takes one velocity for each cell, up to 3000 cells, and prints the summary stats at the end of the run 11 REM this program takes 0.5 samples/sec, and when complied about 6-8 samples/sec
15 DIM FLDS (10)
20 BEEP

```
30 SCREEN 0, 1, 0: COLOR 7: WIDTH 80
40 INPUT "Please enter range maximum"; RANGEMAX:BEEP
50 INPUT "Please enter range number"; RANGE%:BEEP
60 INPUT "Please enter frequency shift"; FREQSHIFT:BEEP
70 INPUT "Please enter the number of samples"; REPETITIONS: BEEP
80 BANDWIDTH=0*8: RBA%=4*32
90 INPUT "Please enter disk drive & data file name"; FILES
100 DIM VEL (1000): MARKER=-99
110 PARAM$="INIT/1/&H200/P/":GOSUB 640
120 PRINT TIME$: BEEP
130 TOTAL=0: Total 1=0: STAND=0:STAND1=0: POSITIVE -0
140 FOR TIME=1 TO REPITITIONS
150 DATA.STRING$=CHR$ (RBA%=BANDWIDTH+RANGE%)
160 PARAM$="WR.STR/12//EOI":GOSUB 640
170 PARAM$="UNLISTEN/"GOSUB 640
180 PARAM$="TALK/12/": GOSUB 640
190 PARAM$="MLA/": GOSUB 640
200 PARAM$="GTSB/":GOSUB 640
210 FOR I=O TO 4 STEP 1
220 PARAM$="RD.BYTE/": GOSUB 640
230 IF LAST%=TRUE% THEN 250
240 D%(I)=DAT%
250 IF DAT%=256 THEN 270
260 NEXT I
270 PARAM$="TCSY/": GOSUB 640
280 IF (D%(3) AND 32)=0 GOTO 150
310 V=((D%(2)=D%(1)/256)/256) * RANGEMAX:VEL(TIME)=(FREQSHIFT-V) *.00196
320 IF OLDVEL=VEL (TIME) THEN 150
330 OLDVEL-VEL (TIME)
340 PRINT TIME, "VELOCITY=", VEL (TIME)
360 NEXT TIME
361 FOR A=1 TO REPITITIONS
362 TOTAL=TOTAL+VEL(A): TOTAL 1=TOTAL1+ABS(VEL)(A)
363 STAND=STAND+(VEL (A) 2):STAND1=STAND1+(VEL(A) 2)
364 IF VEL (A) 0 THEN POSITIVE=POSITIVE+1
380 TIME1=TIME-1
390 MEAN=TOTAL/TIME1:STANDDEV=SQR ((STAND-(TOTAL 2/TIME1))/(TIME1-1))
400 MEAN1=TOTAL1/TIME1:STANDDEV1=SQR((STAND1-(TOTAL1 2/TIME1))/(TIME1-1))
405 NEXT A
407 LPRINT:LPRINT:LPRINT DATE$,:LPRINT TIME$:BEEP:DA$=DATE$:TI$=TIME$
410 LPRINT "MEAN (numeric)="MEAN;TAB(40) "Standard deviation="STANDDEV
420 LPRINT "MEAN (absolute)='MEAN1; TAB(40)"Standard deviation="STANDDEV1
430 LPRINT TAB(40)"trials="TIME1, "positive values="POSITIVE
440 INPUTR "DO YOU WANT THIS RUN SAVED (Y/N)?;Y$
450 IF Y$="no" OR Y$="N" THEN 590
460 BEEP
470 INPUT "ENTER REFERENCE NUMBER FROM BOOK"; CODE%
480 LPRINT "reference number "CODE%
490 PRINT :PRINT :PRINT
500 OPEN FILES FOR APPEND AS #1
520 WRITE #1,CODE%,REPITITIONS
530 FOR Y=1 TO REPITITIONS
540 #1,VEL(Y)
550 NEXT Y
560 WRITE #1,DA$,TI$MEAN,STANDDEV,MEAN1,STANDDEV1,POSITIVE,RANGEMAX, FREQSHIFT,MARKER
570 CLOSE 1
580 BEEP:BEEP:PRINT:PRINT
590 INPUT "Do you want another run (y/n)";O$
600 IF O$="N" OR O$="N" THEN PRINT "Thank you":END
610 GOTO 120
620 END
```

ECOLOGICAL STUDIES

Figure 5:
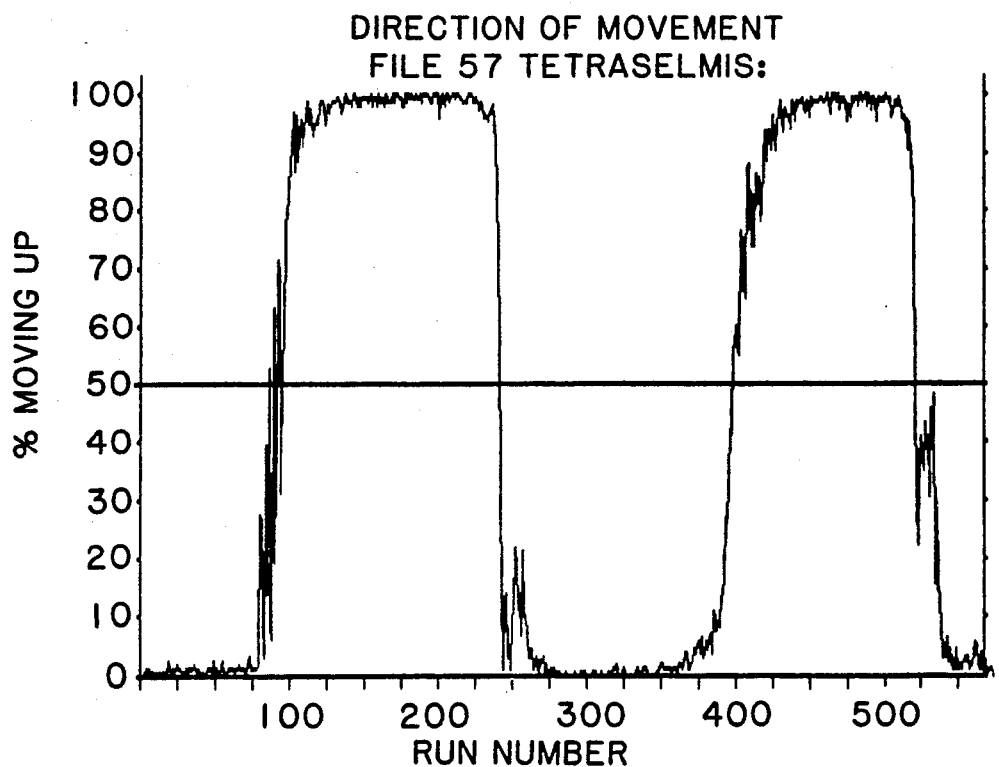
FIG. 5 illustrates the circadian cycle of *Tetraselmis* microbiota.

Using the apparatus and techniques described above, the circadian or natural rhythm of the algae Tetraselmis was recorded, as is disclosed in FIG. 5. The effect of various stimuli can be studied by applying such stimuli alone or coincidentally at a known point in the circadian cycle. Thus, the invention provides very rapid non-destructive measurements under coincidental stimuli. Two differential laser dopplers, at slightly different frequencies to permit discrimination between each differential laser droppler can be used on the same medium and the stimuli limited to the area of the respective laser doppler crossing zones.

Aqueous cultures or microscopic ecosystems can be stabilized with respect to normally recognized environmental variable such as temperatures, nutrient availability, and illumination. When dynamic equilibrium, these can be examined according to the invention to measure the real-time activity level and growth of the population. In the case of multicomponent samples, the data would become a "fingerprint" of the sample, indicating the species present and the distribution of velocities and relative growth within each species.

Figure 6H:
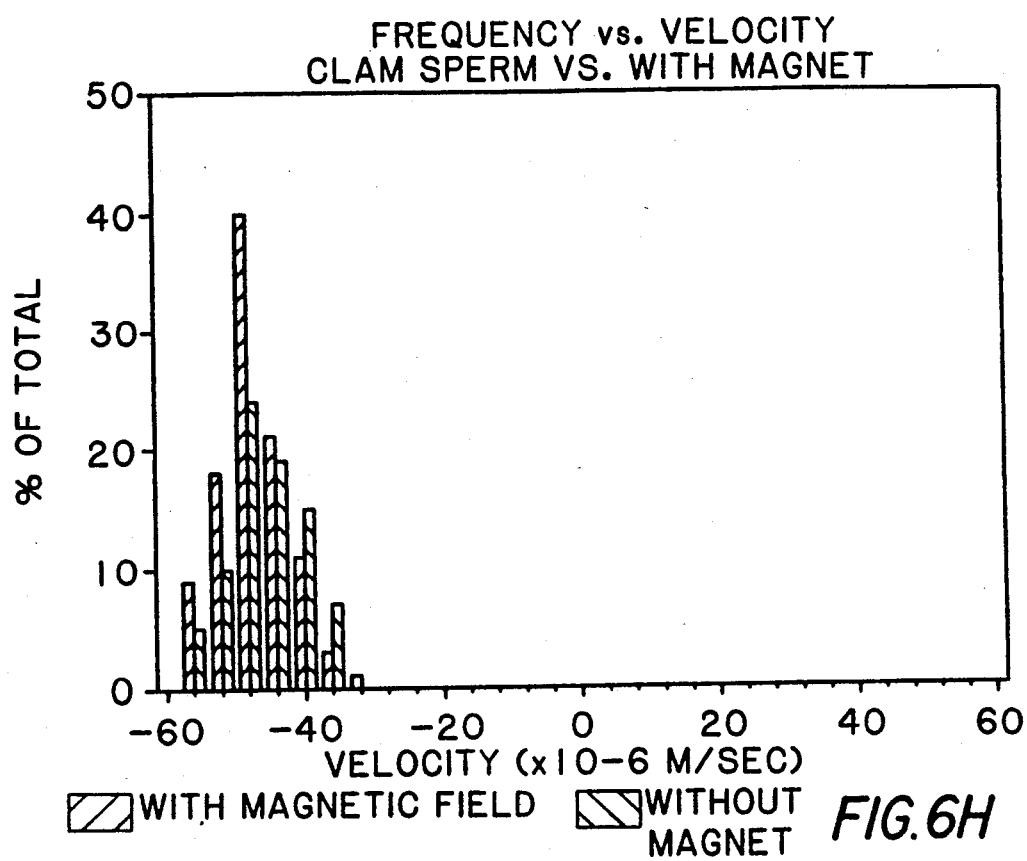
Figure 6I:
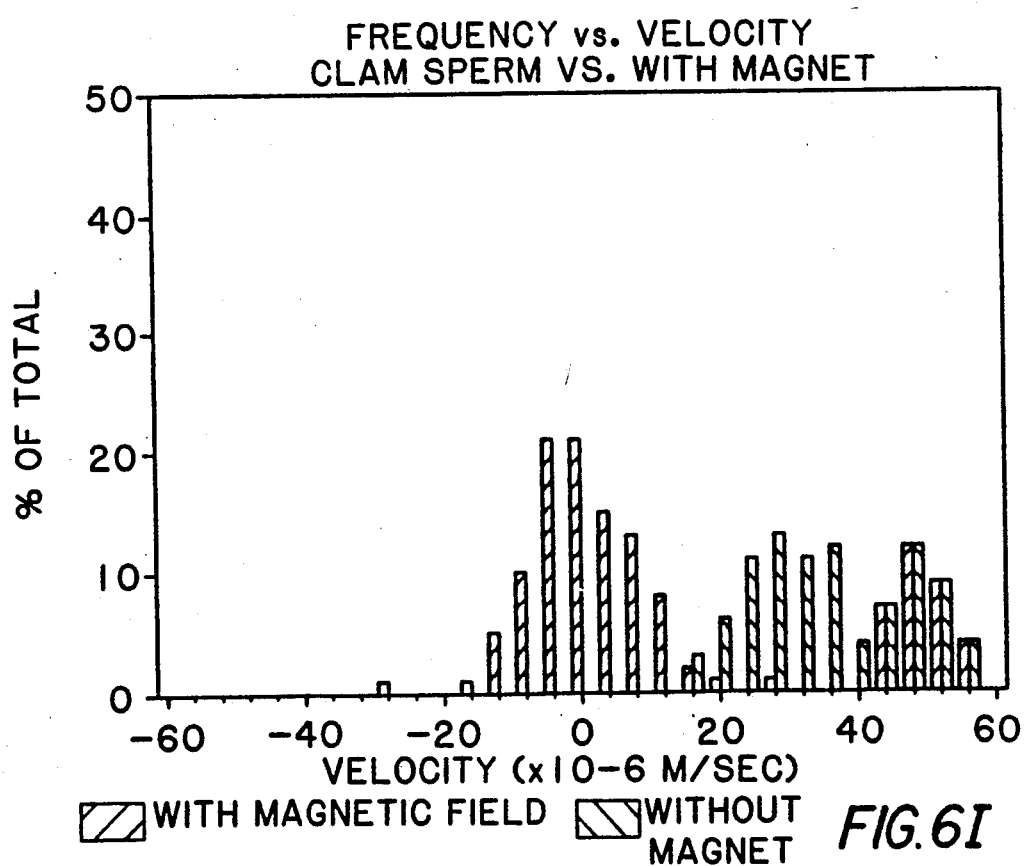
Figure 6J:
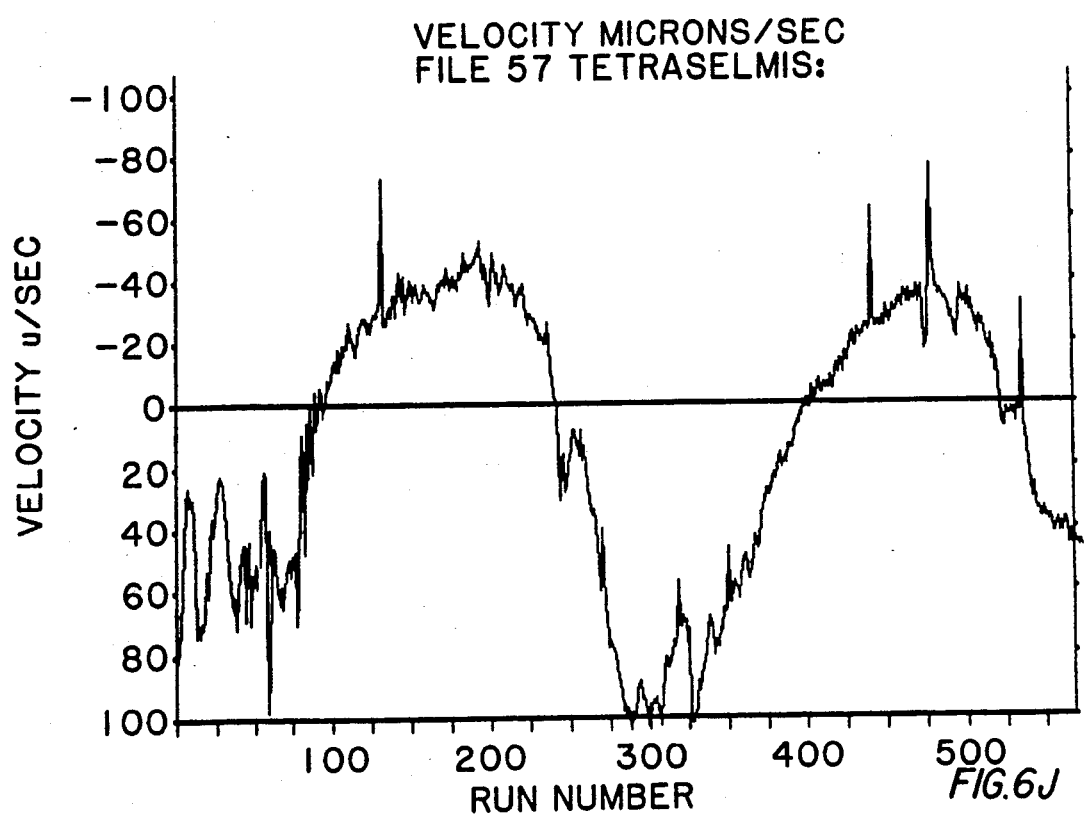
Figure 6K:
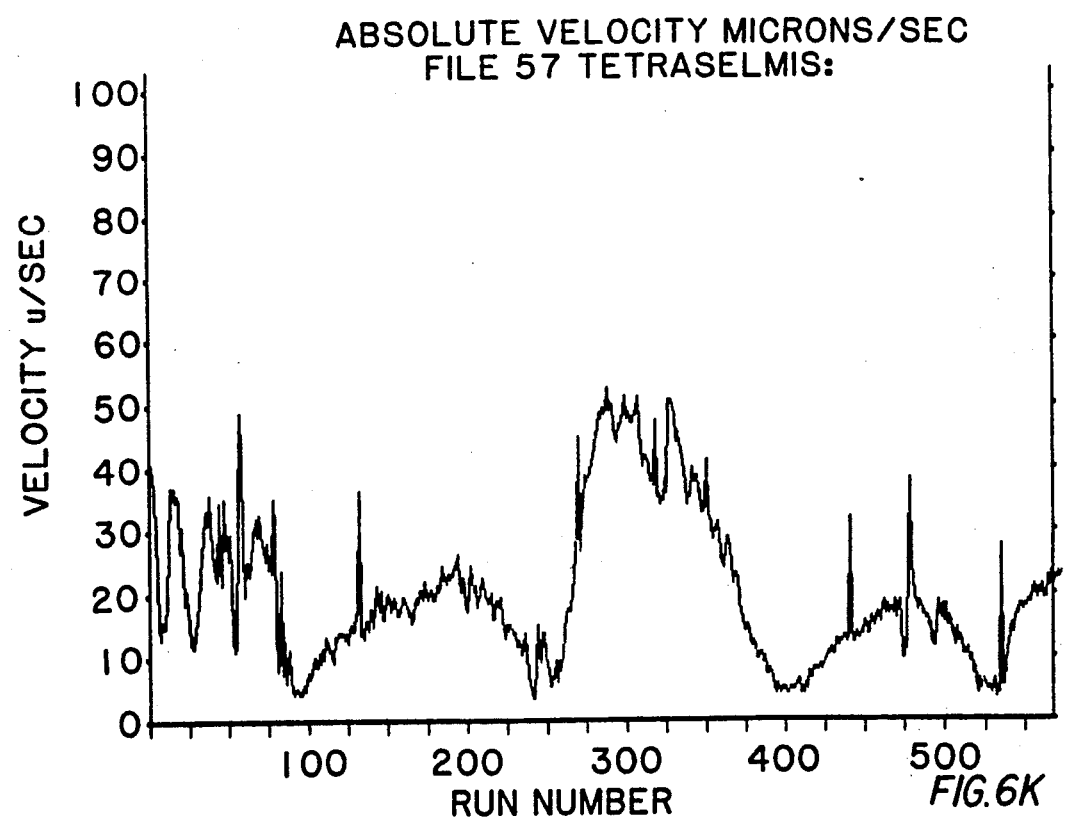
Figure 6A:
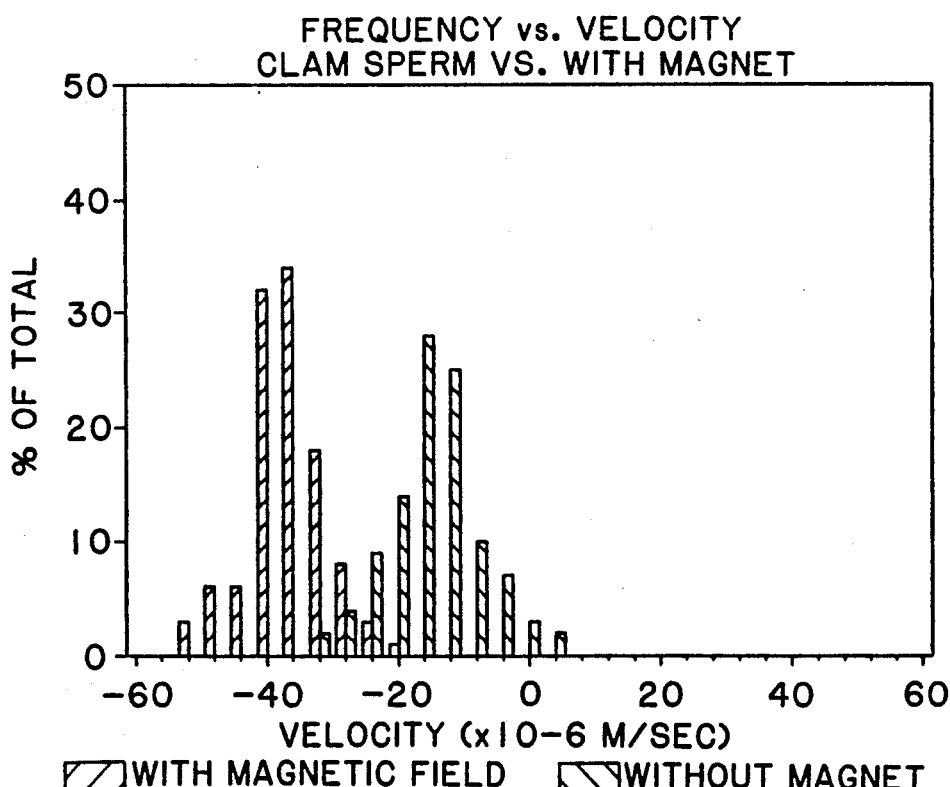
Figure 6B:
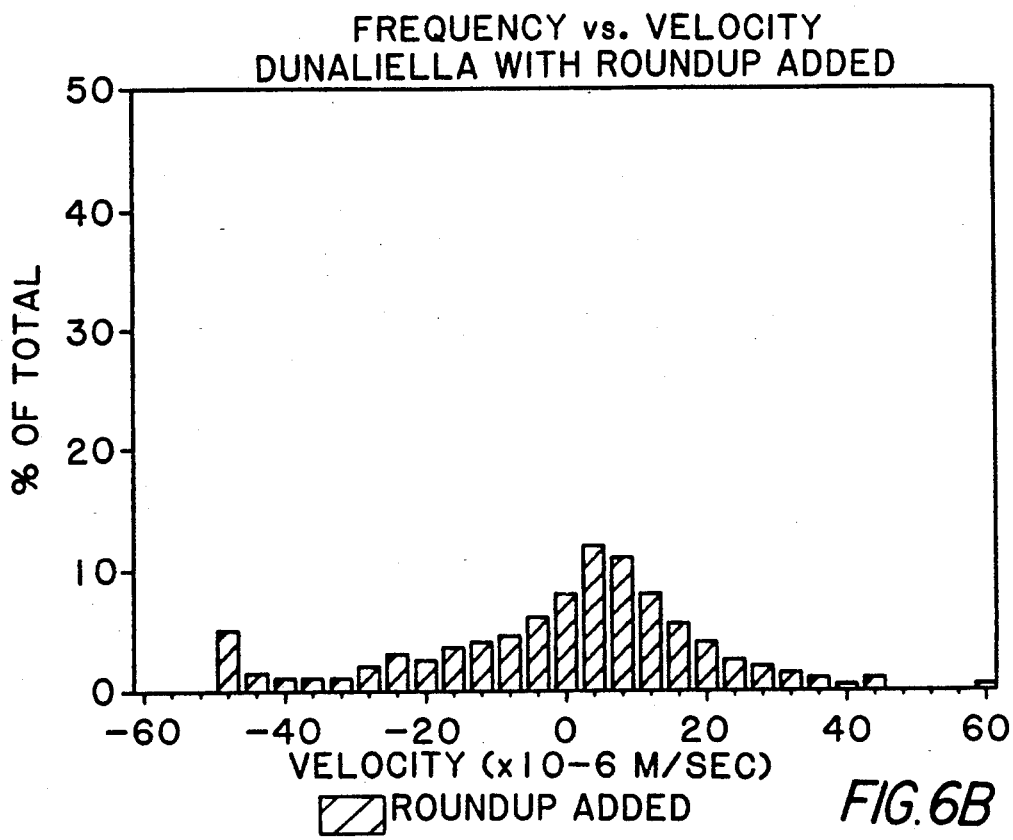
Figure 6C:
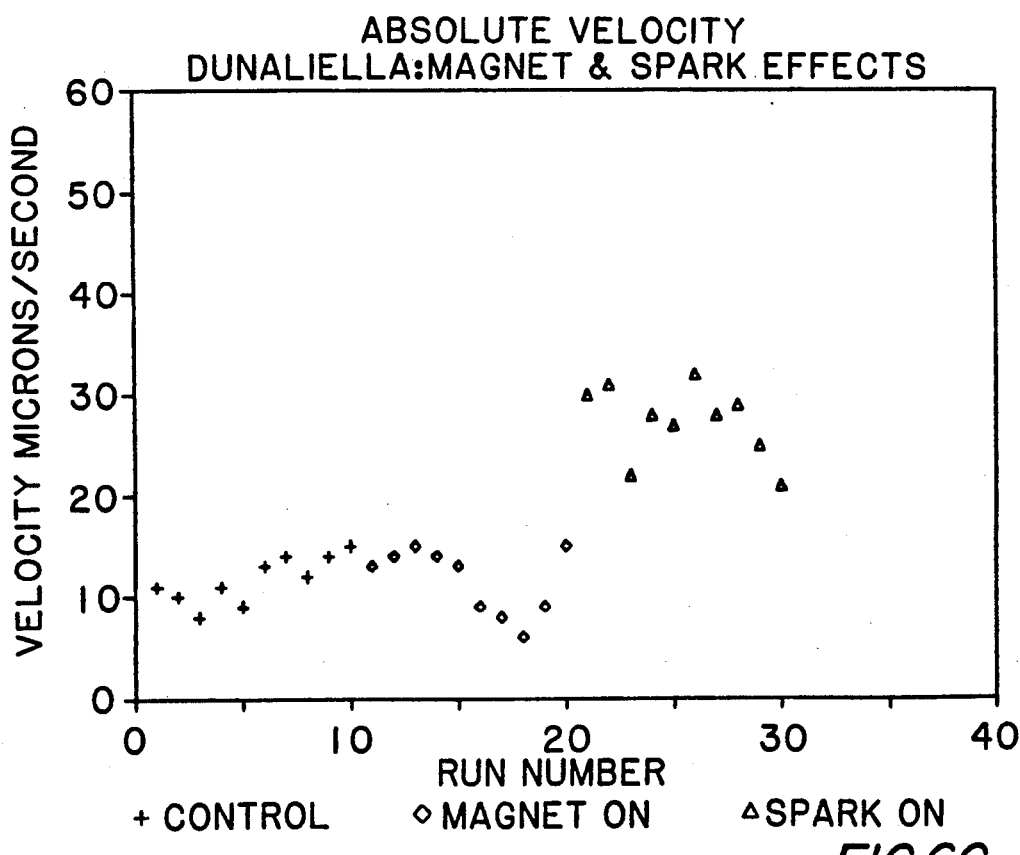

FIG. 6b illustrates the distribution in 1000 measurements of the velocity of the algae Dunaliella, obtained in less than five minutes. In this case a relatively fast moving impurity was present ("IMP" in FIG. 6b) in the culture, swimming upward (negative sign) with a velocity of approximately $50 \times 10^{-6}$ msec$^{-1}$, and two peaks appear in the histogram constructed from the laser doppler data. Finer detail can be developed by increasing the sample number and reducing the width of the bars in the histogram. For ecology studies, there is no prior requirement that each species be identified. The major ones will be evident from microscopic examination. Most importantly, all species present will contribute to the velocity spectra. These spectra can be stored in computer emory 49. Statistical methods can then be used to compare spectra taken in "before and after" experiments.

Trace of analyzed chemical pollutants such as crude oil, herbicides, pesticides or trace metals may be introduced at levels similar to those which the microbiota might experience in their "natural" environment. Nutrients or stimulants may be studied in the same way. Quantitative data on changes in the "motility spectrum" would be recorded, with appropriate statements of the degree of statistical significance.

UTILITY IN CELL MICROBIOLOGY AND MEDICAL SCIENCE

FIG. 6a illustrates the effect of magnetic field from stimuli source 60 on sperm from the clam M. Mercenaria. These data vividly illustrate subtle effects that could not previously be detected by studying plants and animals higher in the food chain or by crude measurement of the total mass of the microbiota. Cellular reproductive behavior is recognized as sensitive to environmental variables such as EM fields, radiation, and the composition of the suspending medium, but no prior art instrument exists which can track the behavior through many generations under the influence of one or more external variables. The invention rapidly produces statistically significant information, and it may become as useful to the microbiologist as the spectrophototomer is to the chemist and physicist.

In addition to the application already described, the device has a most important application in the area of immunology. It can monitor the motility of white blood cells under the influence of a wide variety of exogenous variables, can document the effects of minute changes in composition of the intercellular fluids, and track the degradation or abnormal development of cells under specific conditions.

As the equipment is developed fully, several stimuli may be applied simultaneously at a known point in the circadian cycle.

As shown in FIG. 3, a control signal can be applied to the source of exogenous stimuli 60 on line 61 from computer 48 at predetermined times in the circadian cycle of the microbiota and the effect monitored and recorded almost instantaneously. Such exogenous stimuli can be selected from the following:
a) magnetic field—a magnetic coil is energized by signal or line 61 of FIG. 3,
b) electric field—electric field plates are energized by signal on line 61 of FIG. 3,
c) spark discharge—a spark discharge is energized by signal on line 61 of FIG. 3,
d) x-rays—x-ray source is energized by signal on line 61 of FIG. 3,
e) ultraviolet—an ultraviolet source is energized by signal on line 61 of FIG. 3,
f) infrared—an infrared source is energized by signal on line 61 of FIG. 3,
g) thermal (control of cuvette temperature),
h) variable visible spectrum of light,
i) pressure (vary of fluid medium in which sample microbiota are swimming), and
j) chemical (addition of trace chemicals to the fluid medium).

The stimuli need not be constant, and indeed, in some cases it may be preferred to apply one or more stimuli for a predetermined time and monitor the recovery of the organism, or to alternate the stimuli and monitor the response. Thus, a magnetic stimuli can be applied at a predetermined phase in the natural rhythm of the microbiota and then an optical stimuli applied with the respective responses being monitored. Moreover, the stimuli need not be of constant intensity or dosage, and indeed, variable intensity, variable time period of application are very useful in the analysis of microbiota. There can be several analysis zones in the sample medium with plural differential laser doppler zones for simultaneous application of stimuli (optical and magnetic, for example) on essentially the same microbiota.

OYSTER AND CLAM SPERM; MAGNETIC FIELD EFFECTS PRESENTED AS HISTOGRAMS

After characterizing sperm from the clam M. Mercenaria with a 1000 sample run (FIG. 6f), the standard 25 gauss field was applied. The upward acceleration of the entire population was dramatic. (FIG. 6g) Median velocity changed from $-15 \times 10^{-6}$ msec$^{-1}$ to $-37 \times 10^{-6}$ msec$^{-1}$. In this case there was no detectable induction period. Subsequently, an attempt was made to repeat the experiment with the same sperm suspension. FIG. 6h shows that it appears to sustain the higher velocity distribution; application of the field had no further effect.

The phenomena seems replicable, with small variations which we do not claim to understand. FIG. 6i shows that during the initial characterization (in the absence of field), the population exhibited bimodal behavior. After the application of the field the data initially accumulated in the mode with a peak around $45 \times 10^{-6}$ msec$^{-1}$, but after approximately a minute there was a relatively abrupt change to the distribution at the far left, with a median close to zero.

RHYTHMIC BEHAVIOR IN A PURE CULTURE

Data of FIG. 5 and FIGS. 6j and k are supported by several other very similar sets from extended dark runs with both Tetraselmis and Dunaliella. It is too early to say whether the rhythmic change in the predominant vector is due to short term memory (night/day cycles prior to study) circadian influence, or some other effect such as synchronous division. This algae is known to divide about once a day. The most puzzling aspect is spatial: we know from studies of collids such as dilute milk or dead algae, that there are no detectable convection currents in the cell. With initial concentrations of the order of $0.5 \times 10^6$ per ml, and velocities of the magnitude observed, it is hard to image a mechanism by which continuous upward movement can take place over periods approaching twelve hours unless density variation of division is involved.

Sampling of the cell content and microscopic examination reveals that there really are a reasonable number of live cells in the center of the cuvette at anytime, consistent with the measurements. Visual observation shows a green accumulation at both the top and the bottom of the cell, usually stronger at one or the other.

It is quite possible that synchronous cells division is playing a role. Conceivably, daughter cells could swim down from the surface layer (given a higher density than the parent this would be energetically efficient) and take about half their life to increase in fat and liquid content to the point where they would again rise, ready to divide. This is not presented as a thesis: we are opening a new work area, and are privileged to be able to make original observations. Hurried explanations of the observations are inappropriate.

Referring collectively now to FIGS. 7a to 7p and 7r to 7z, the processing of this data differs from that of FIGS. 6a–6l in that FIGS. 6a–6l used a sixteen (16) bit number to define velocities whereas the series (FIGS 7 series) used an eight (8) bit number which could be processed more rapidly than the sixteen bit number and was processed by a somewhat different computer program than the laser 16. This is a manifestation of trade off between accuracy, range and speed. The limits are set by the speed and accuracy of the equipment used to monitor the doppler frequency (virtually unlimited resolution (in a biological context) can be obtained when using faster frequency counting equipment) and by the interrelated variables which can be selectively controlled by the user, run time, range and resolution within each range. This is analogous in some ways to conventional spectrometry, where rapid scan of wide spectral regions can be followed by detailed examination of regions in the spectrum of particular interest and assignment of lines within the selected regions.

The following illustrates and corrolates the ranges to frequency:

| Range | kHz | | | |
|---|---|---|---|---|
| 1 | 10 | 100 | 1000 | 10,000 |
| 256 Bytes | 256 Bytes | 256 Bytes | 256 Bytes | |

(an eight byte number in this case)

Within any range, the shift (5.5, 50, 500, 5000) is placed and then the doppler line broadening around that shift is monitored and recorded. The first three digits are the byte numbers (out of 256) giving the peak in the frequency space the numbers after the comma are the number of times frequencies fell in that slot.

FIGS. 7a to 7d illustrate frequency distribution in each range, with the shifts and immediately adjacent low velocities removed. With two beams recording only one vector, such low velocities are not so distinctive, since faster particles may cross the measuring volume at low angles. However, with three beam pairs, according to the invention, one can obtain unique assignments for every frequency measurement and track three dimensionally.

FIGS. 7e to 7h provide illustrative comparisons of the frequency spectrum of *Dunaliella* (FIGS. 7e and 7h) and *Tetraselmis*.

Figure 7A:
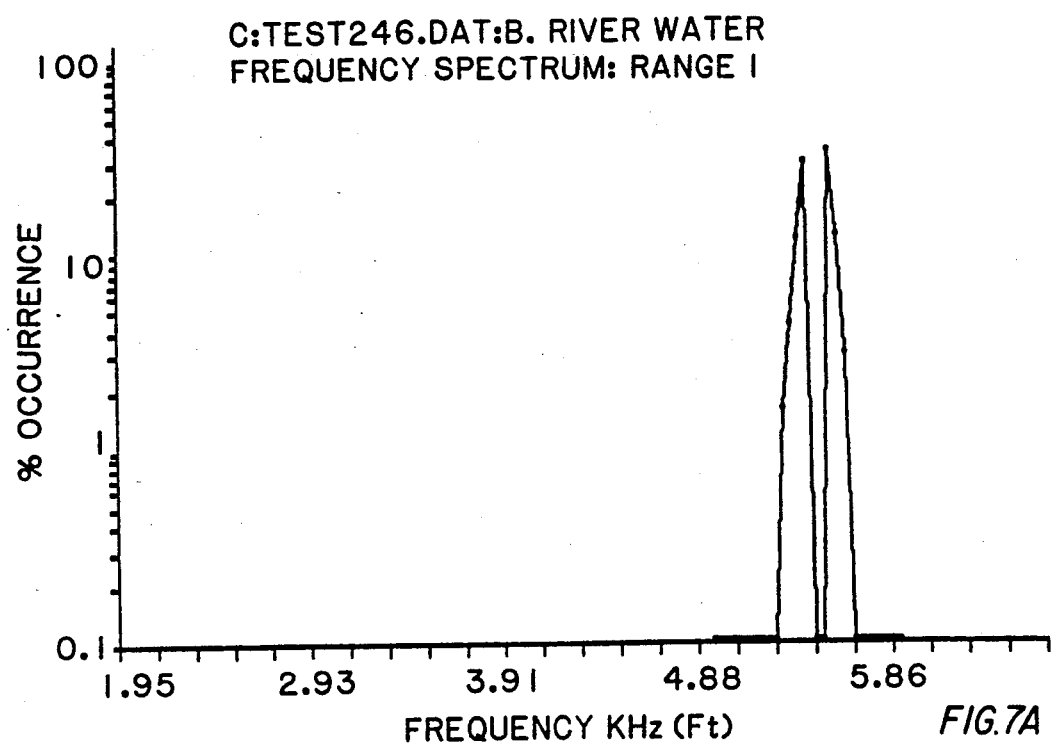
FIGS. 7a through 7p and 7r through 7z are further histograms which describe a community of microorganisms, including phyloplanton and zooplankton, taken from the broadkill river at Lewes, Del. and examined by the invention herein.
Figure 7B:
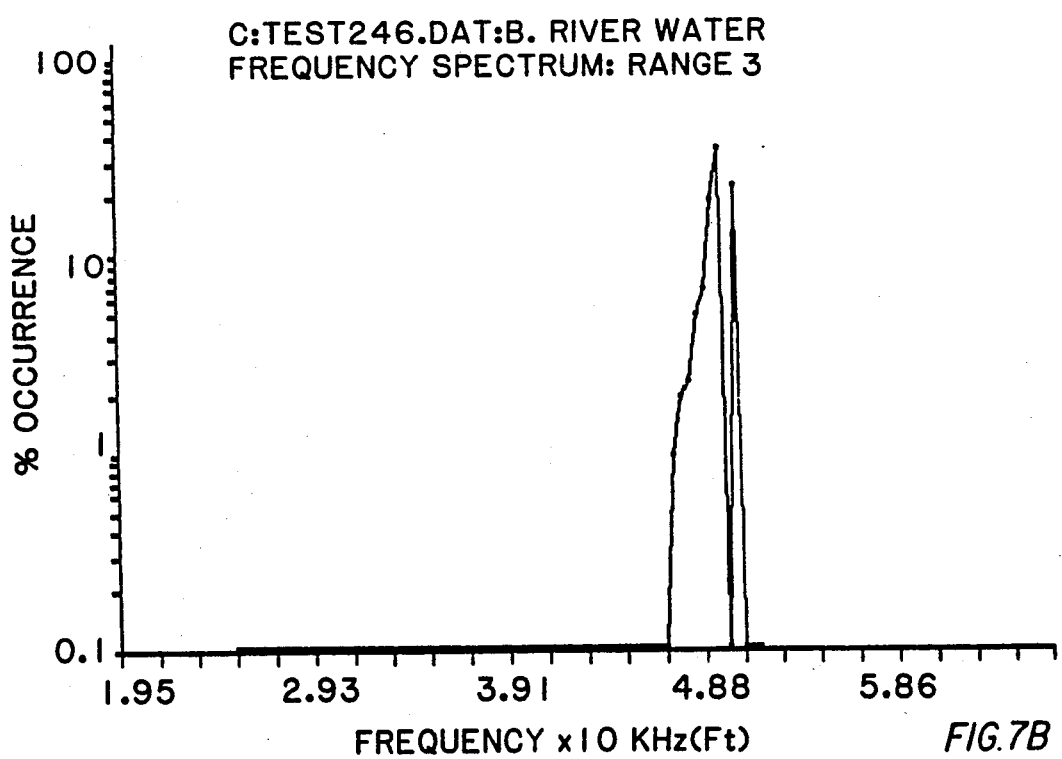
Figure 7C:
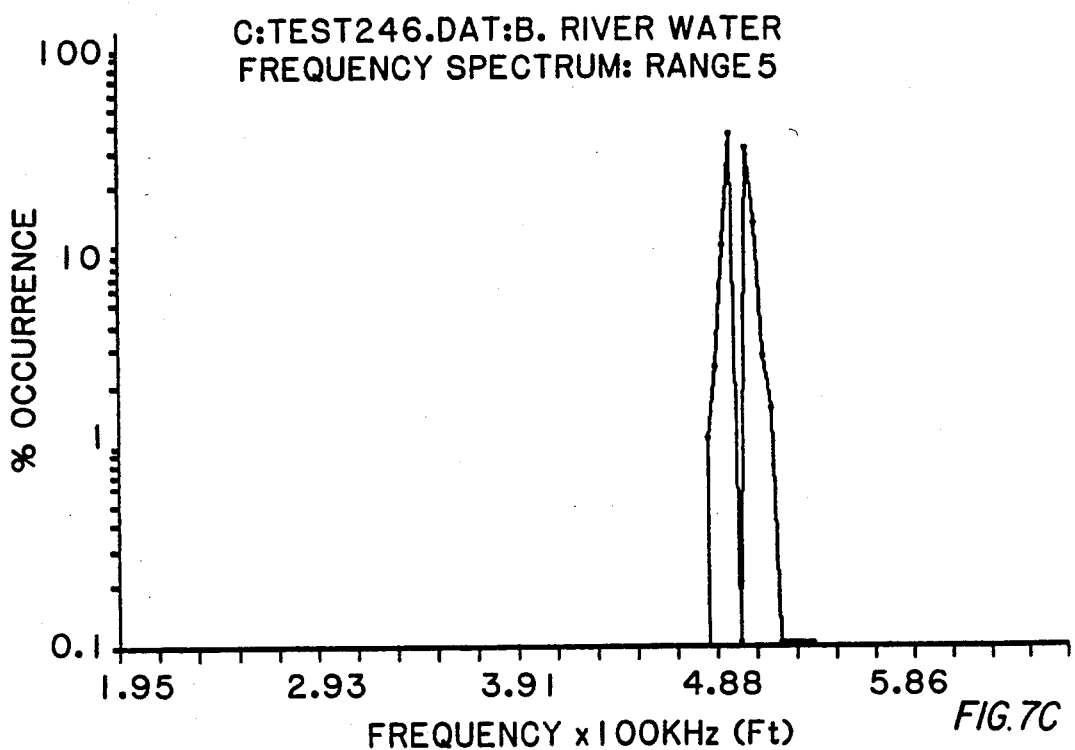
Figure 7D:
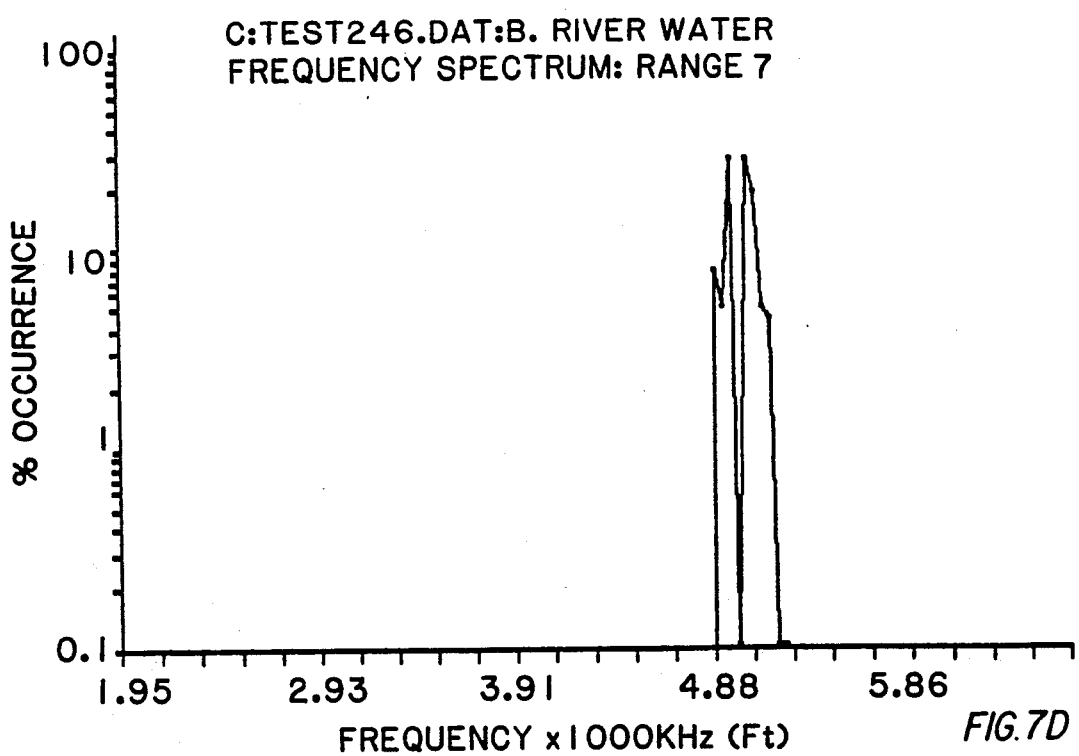
Figure 7E:
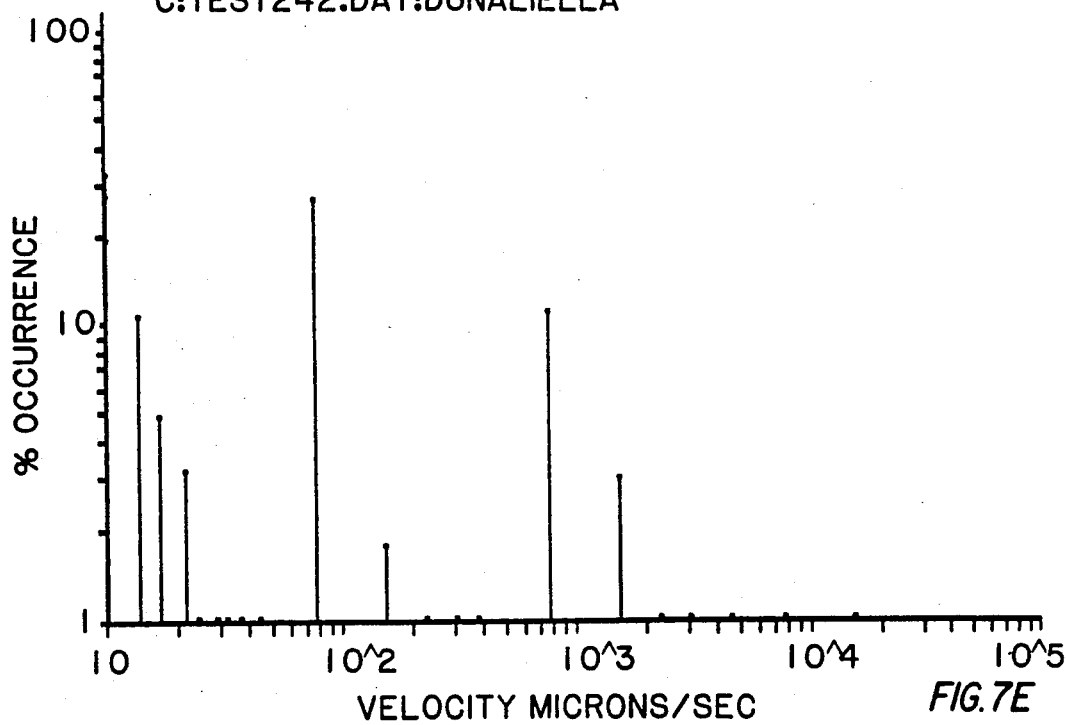
Figure 7F:
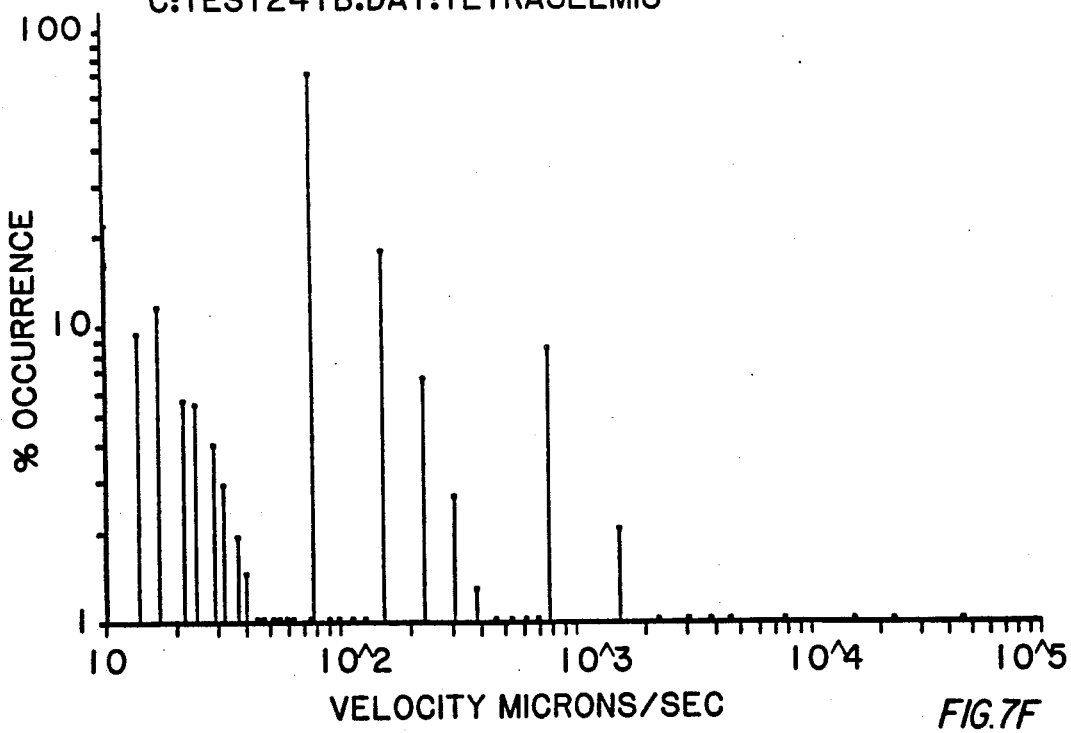
Figure 7G:
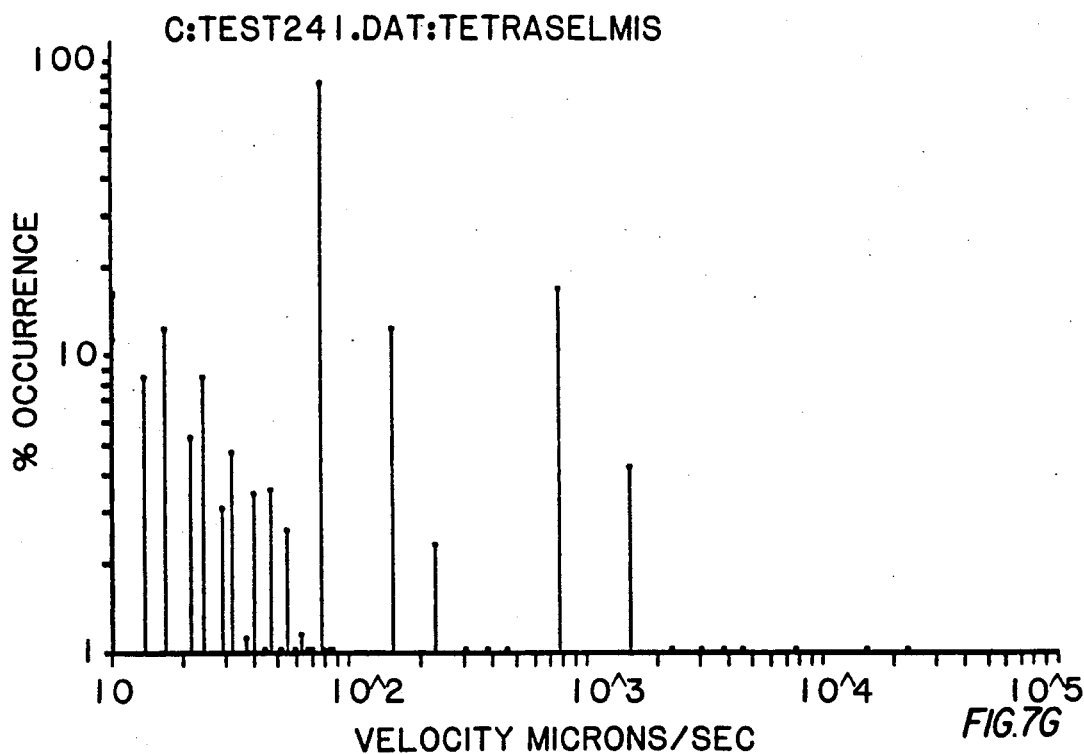
Figure 7H:
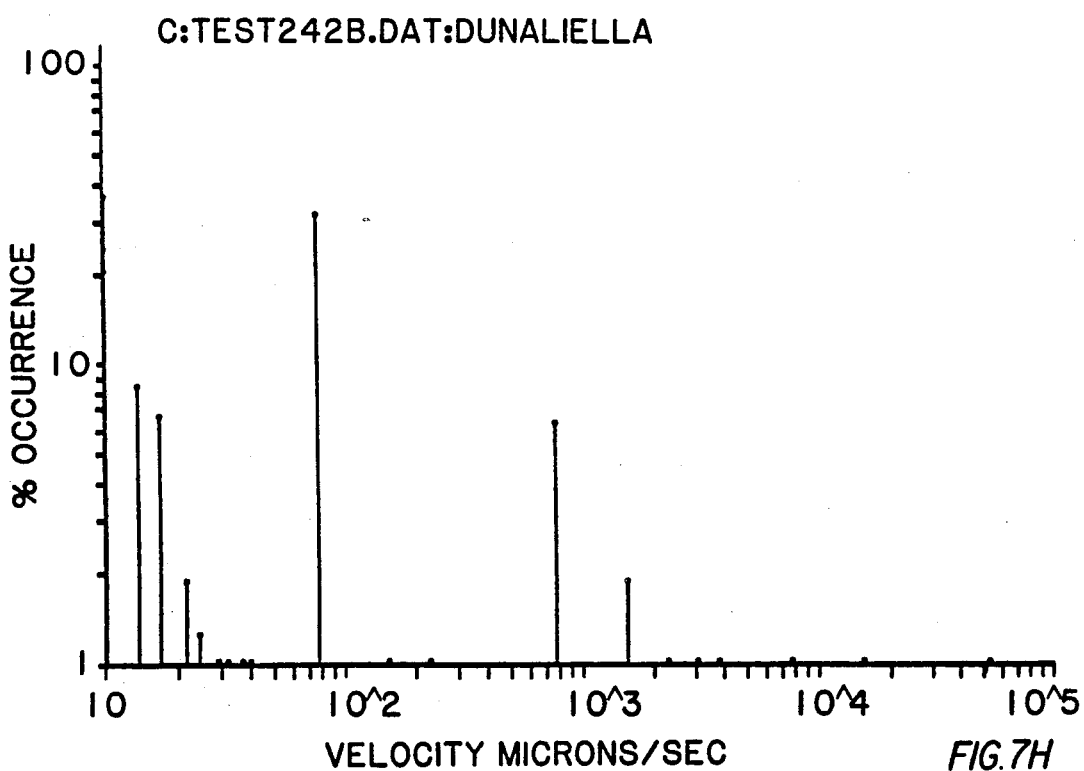
Figure 7I:
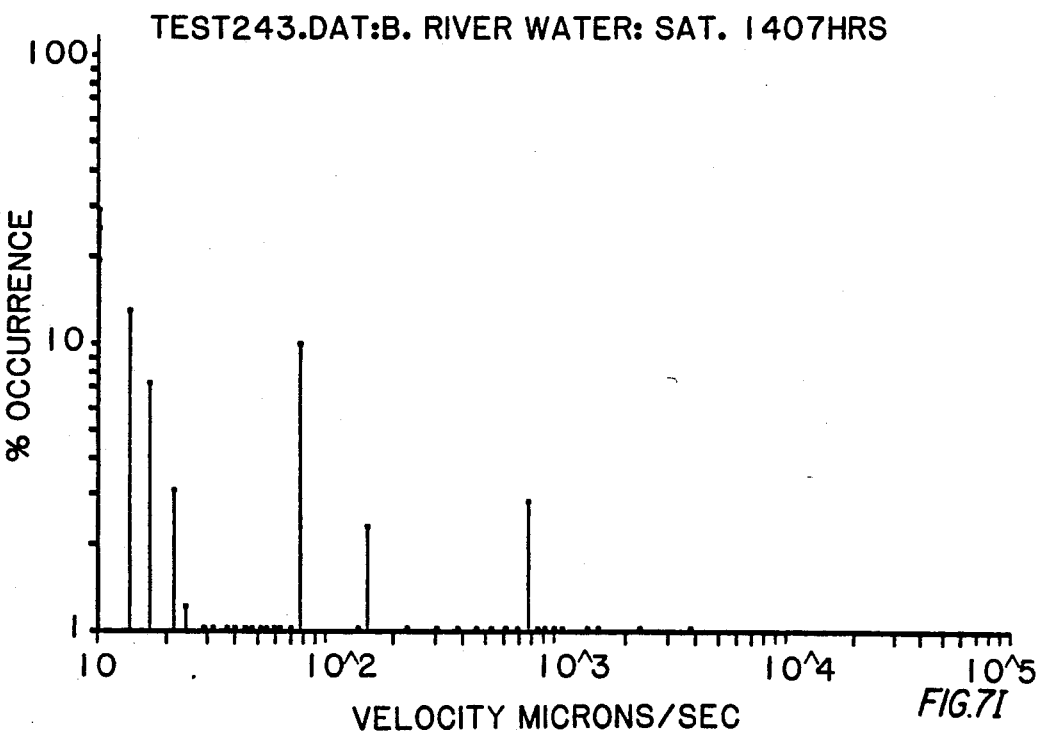
Figure 7J:
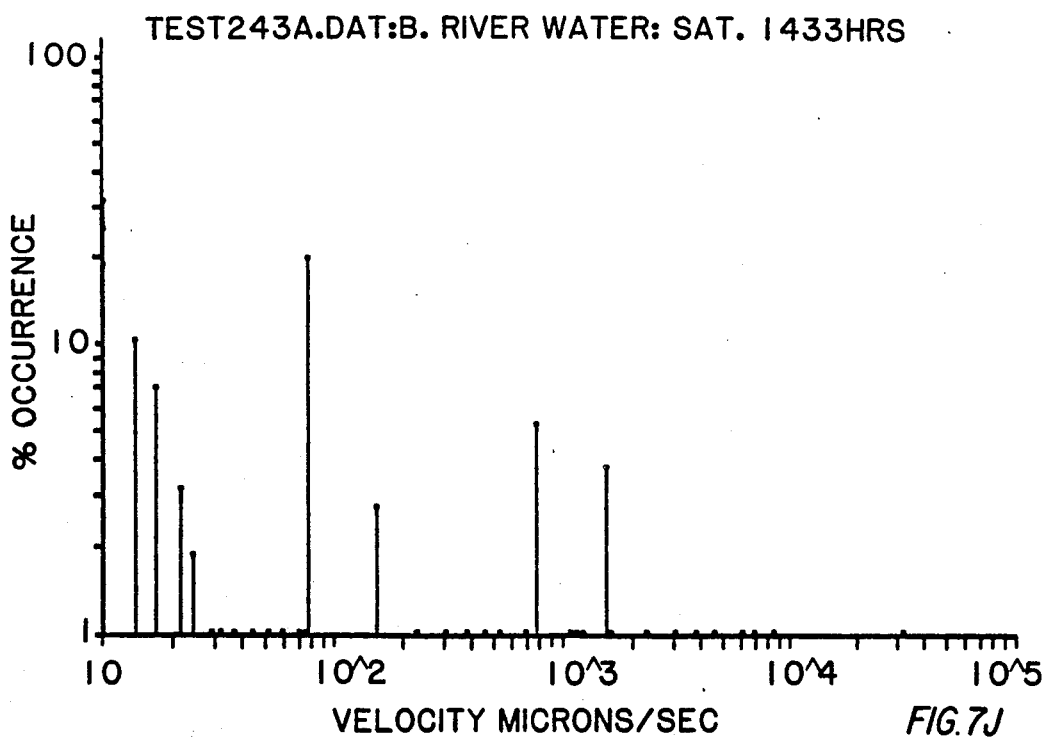
Figure 7K:
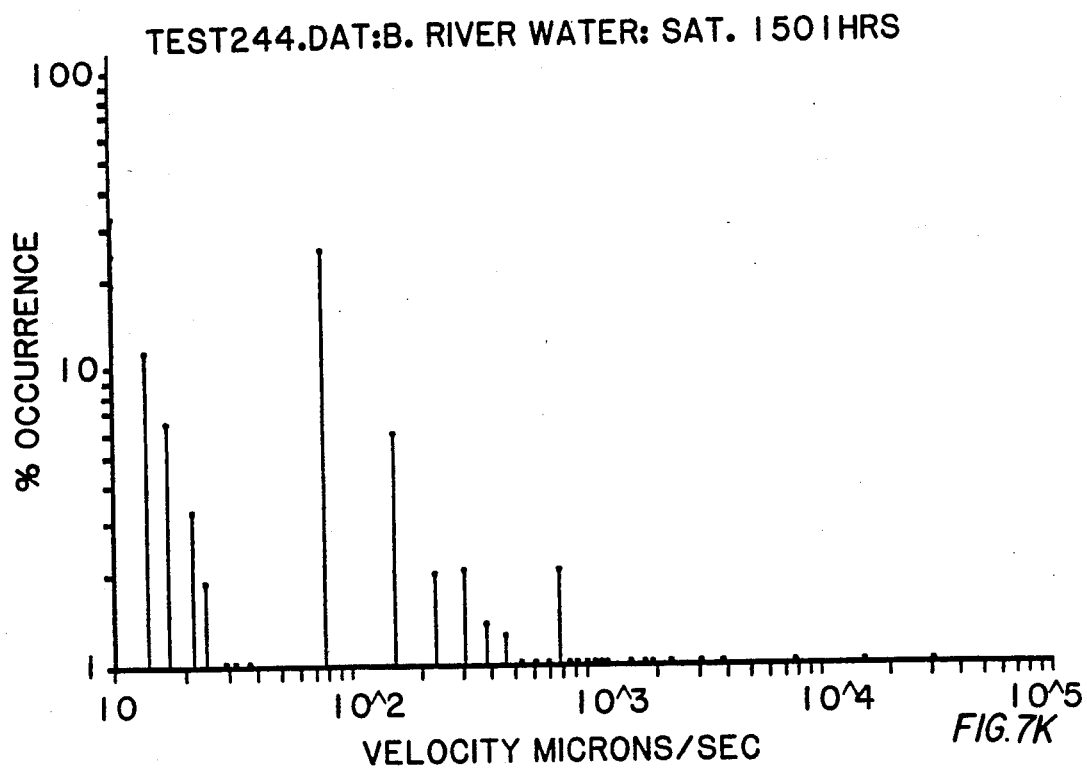
Figure 7L:
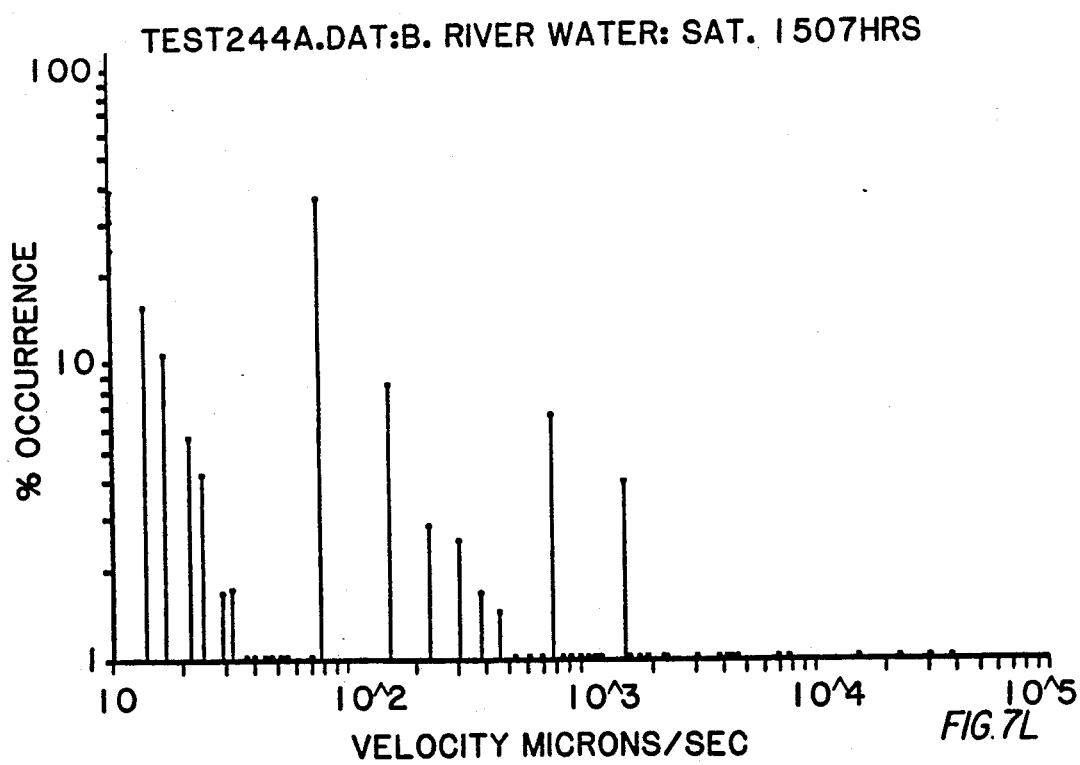
Figure 7M:
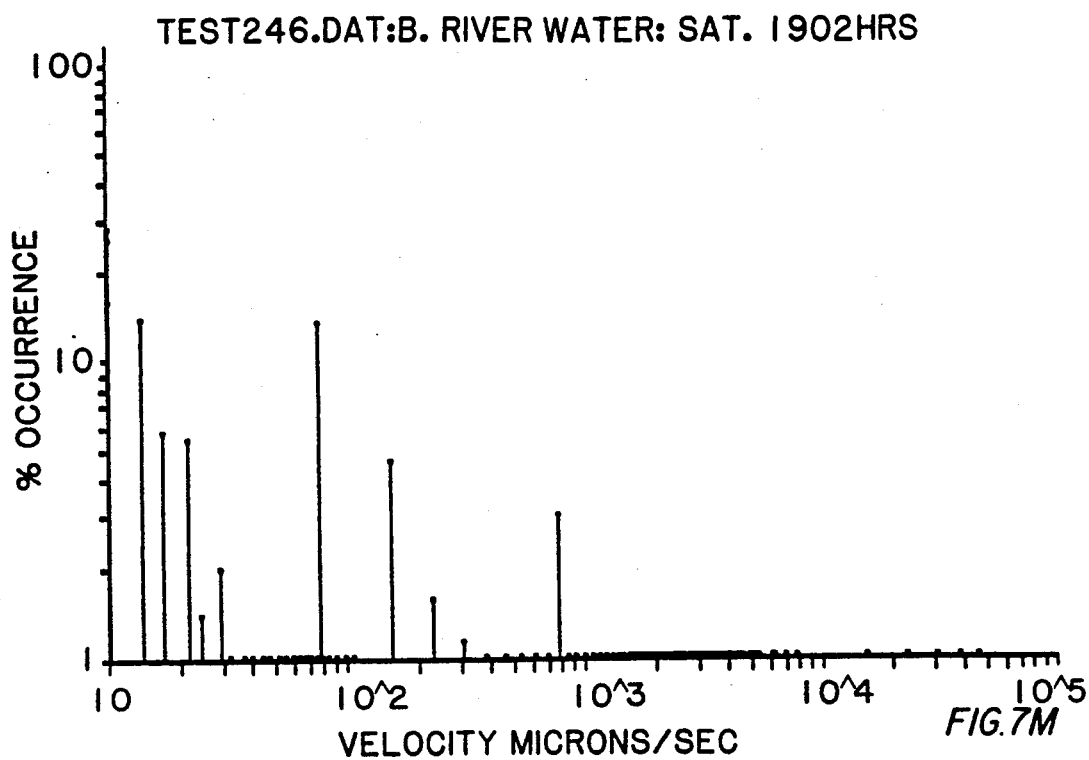
Figure 7N:
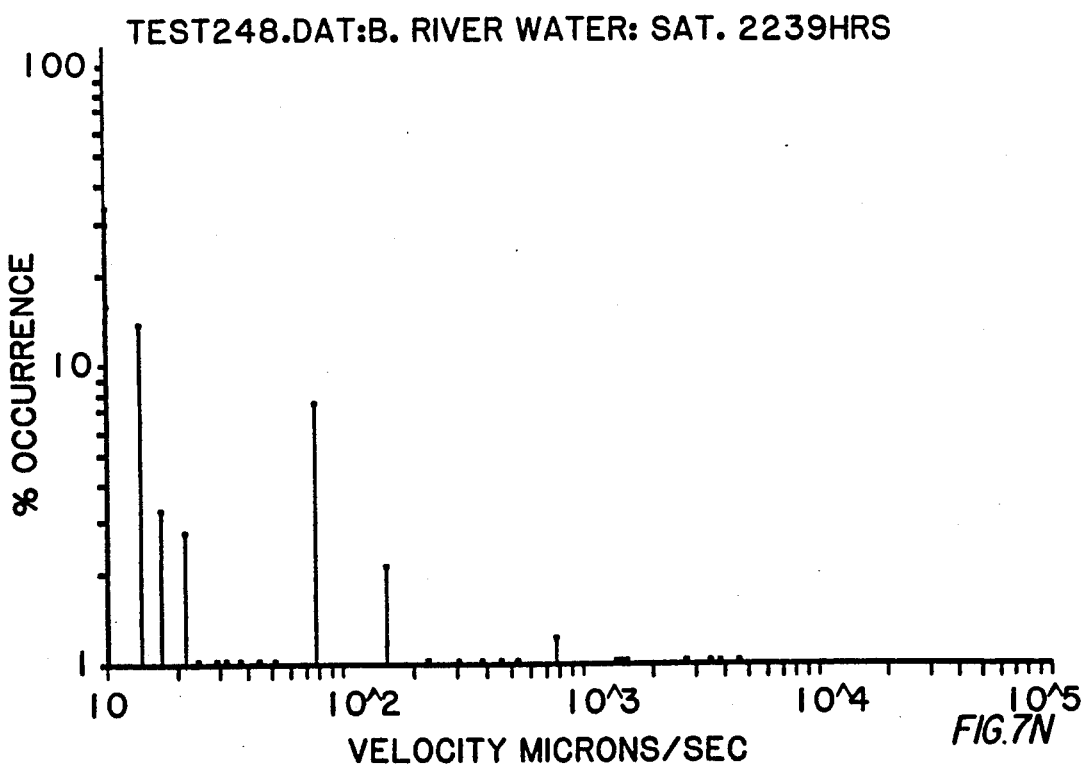
Figure 7O:
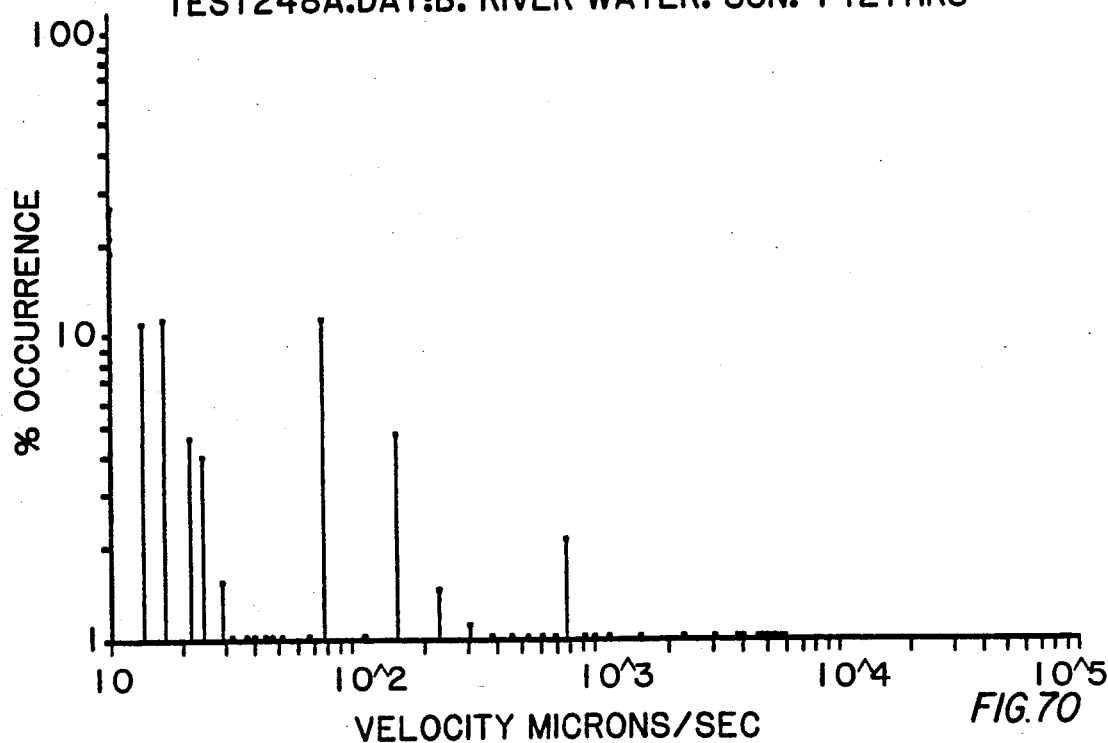
Figure 7P:
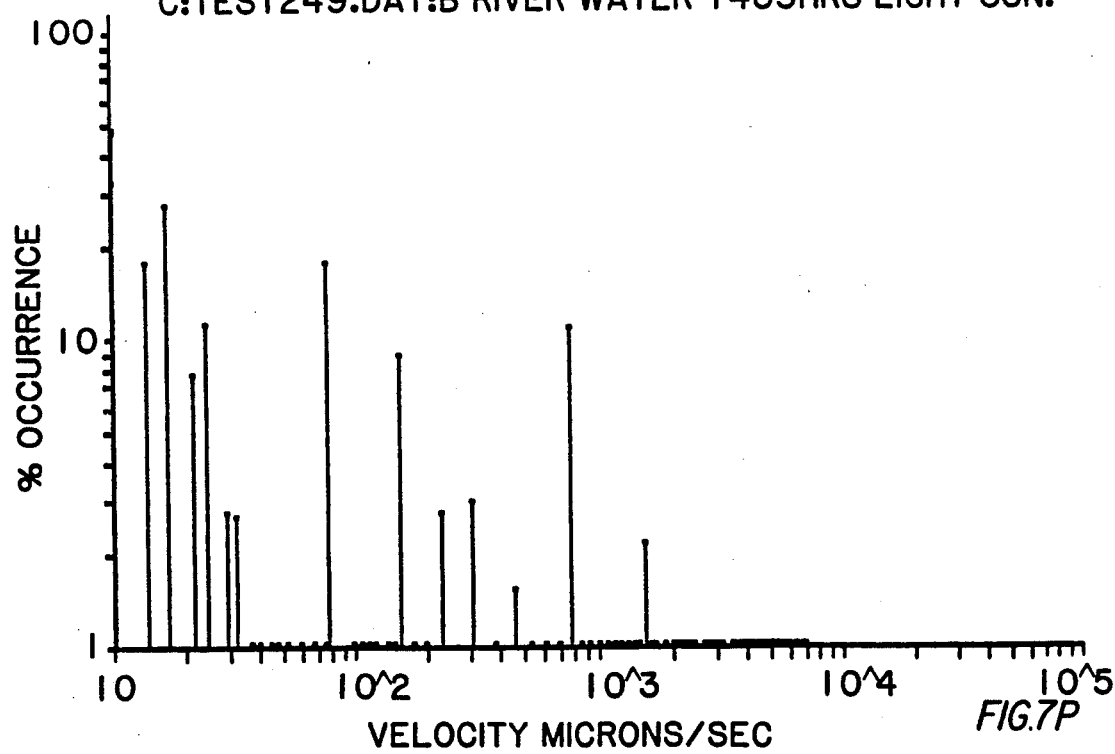
Figure 7V:
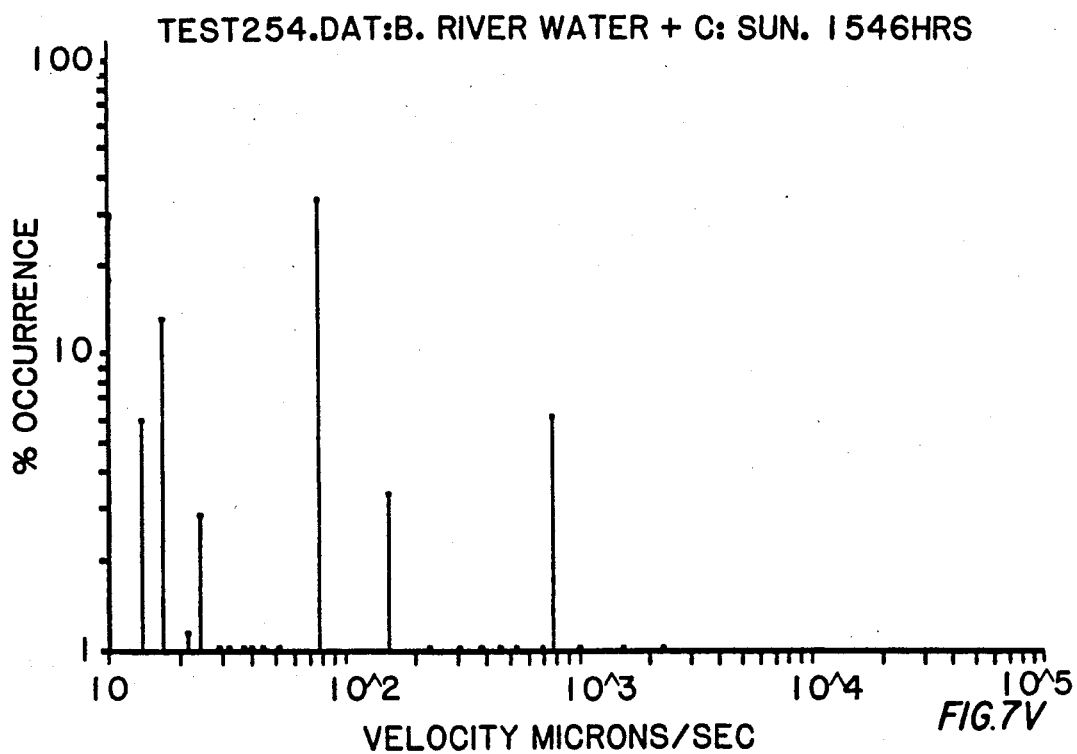
Figure 7W:
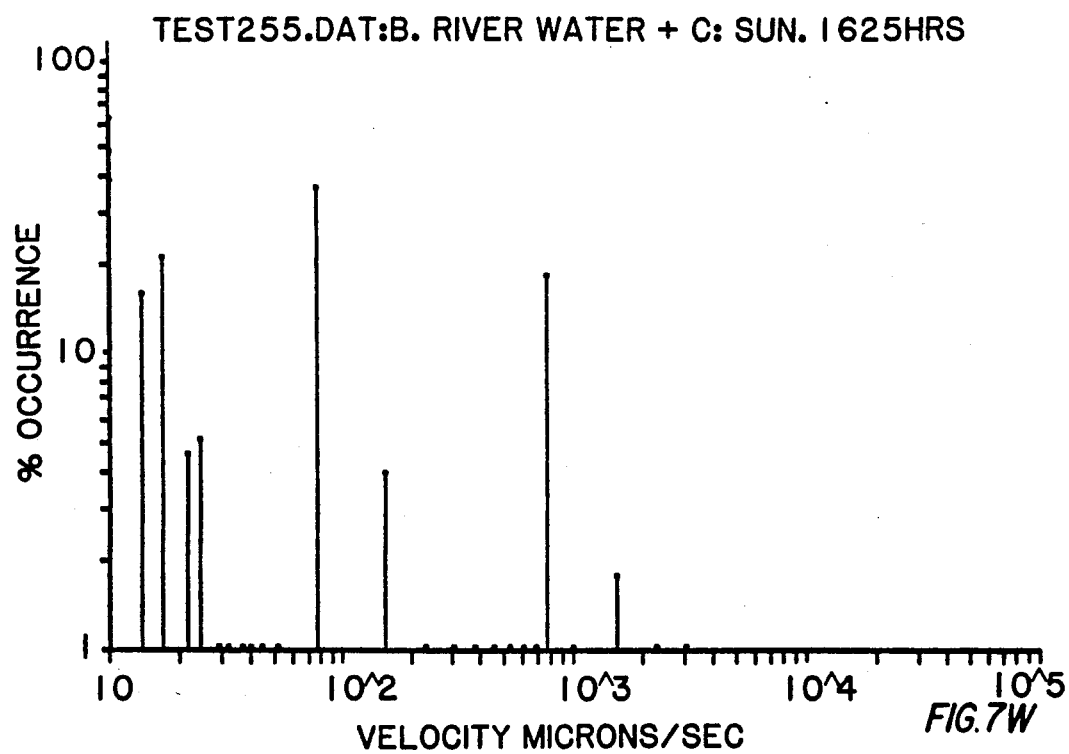
Figure 7X:
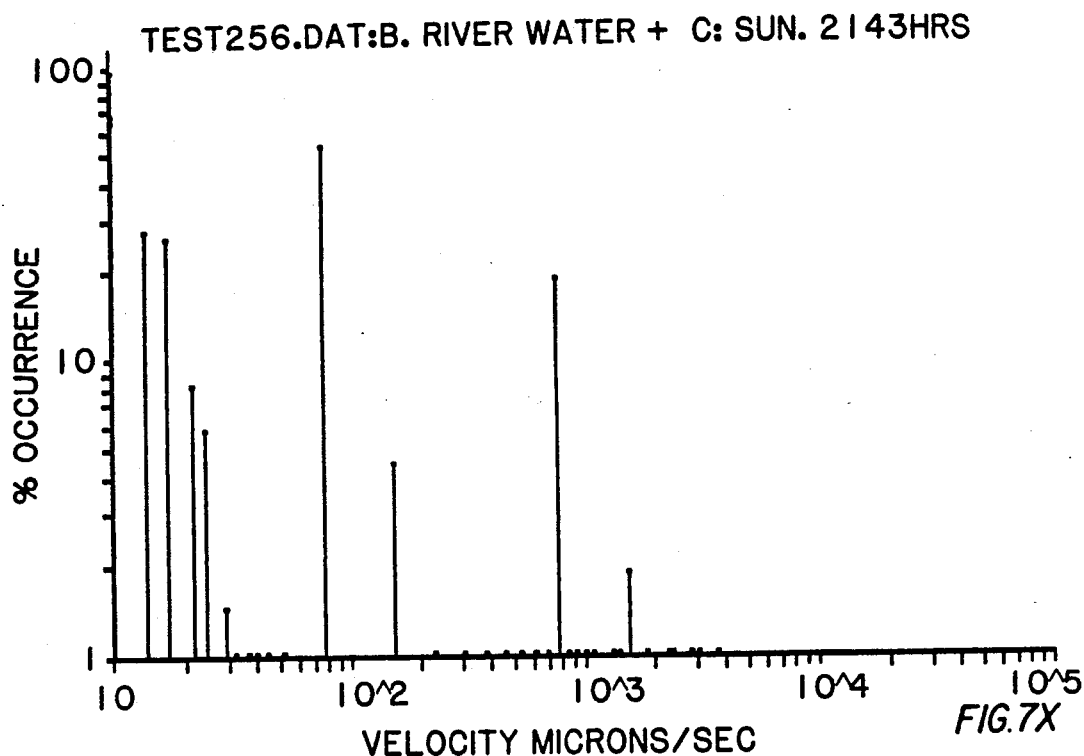
Figure 7Y:
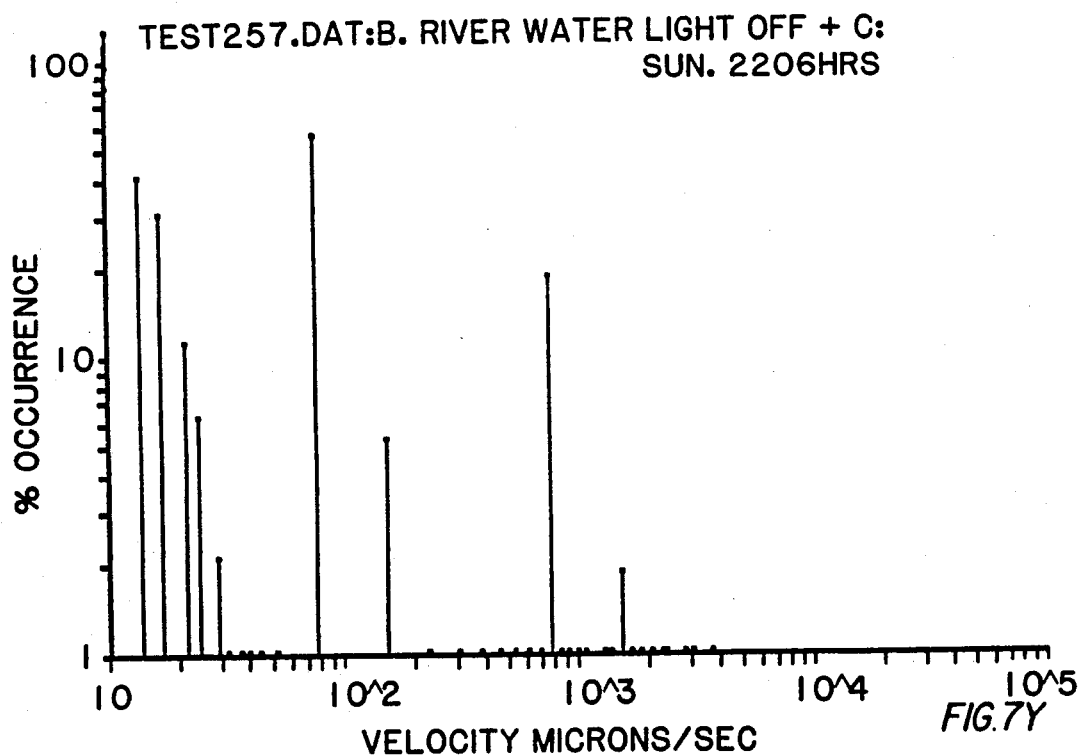
Figure 7Z:
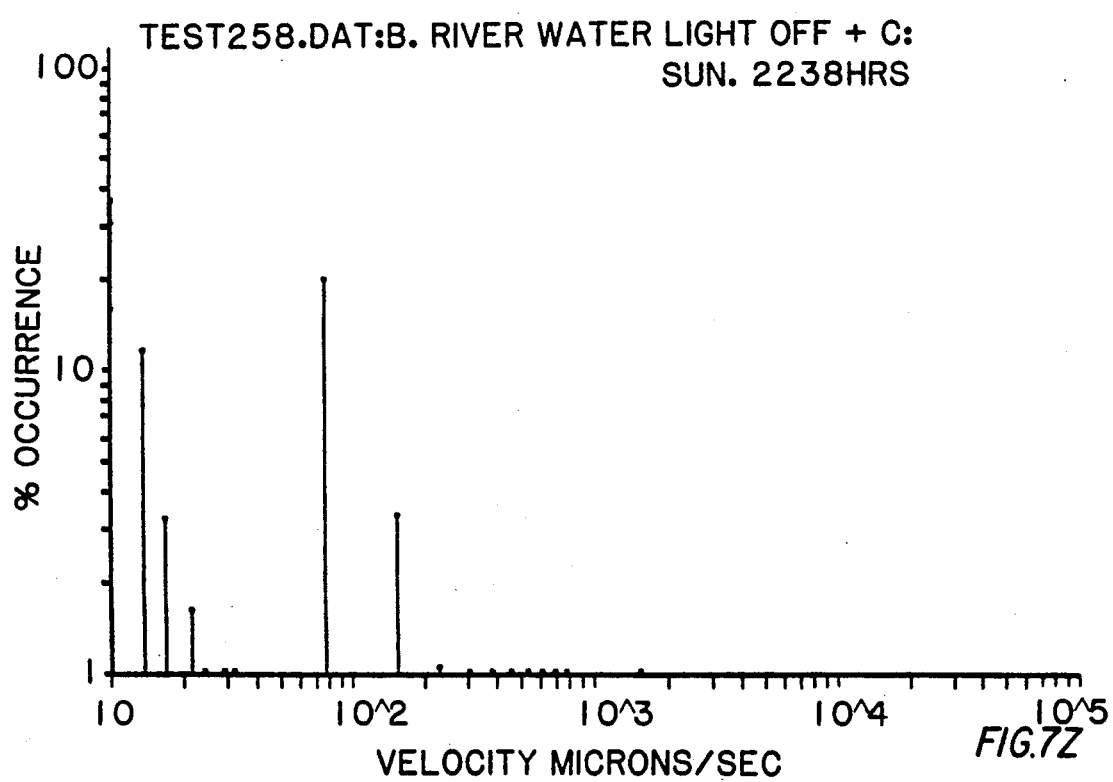
Figure 7T:
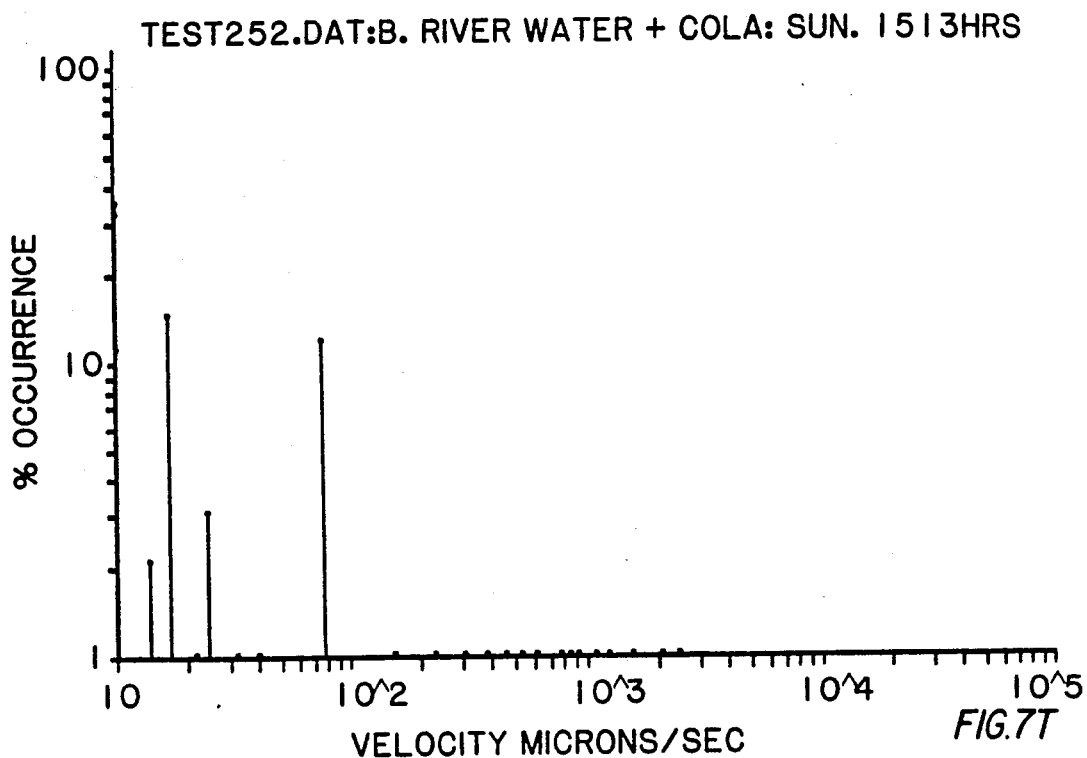
Figure 7U:
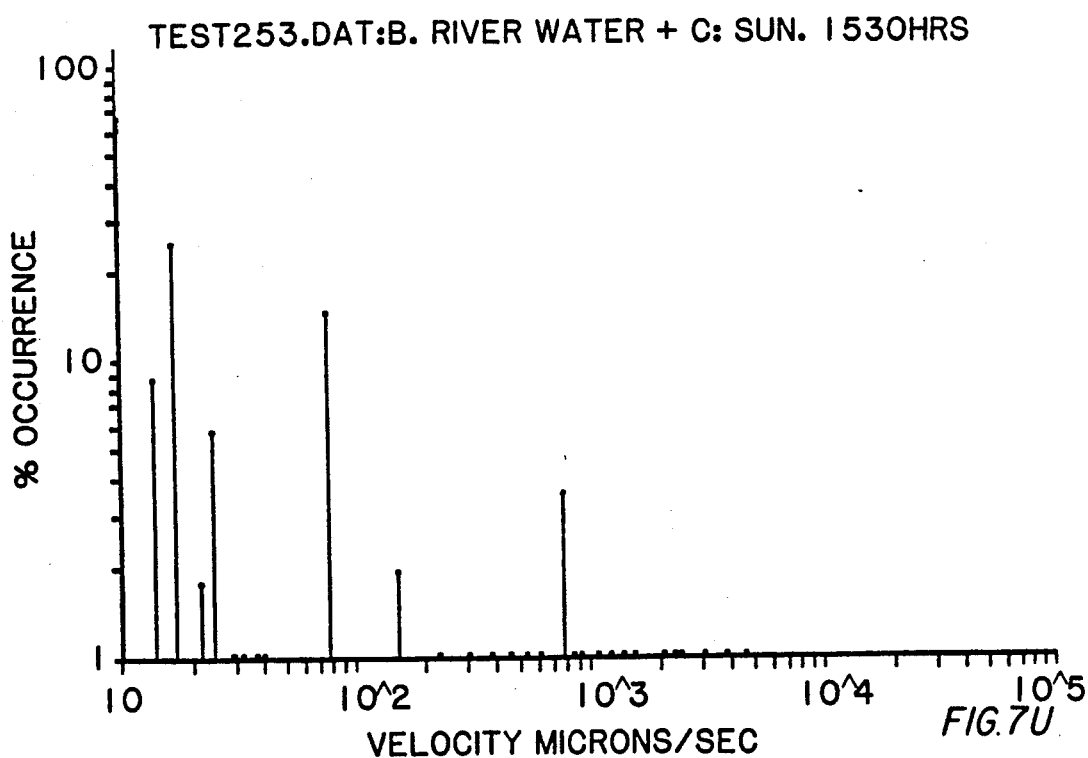
Figure 7R:
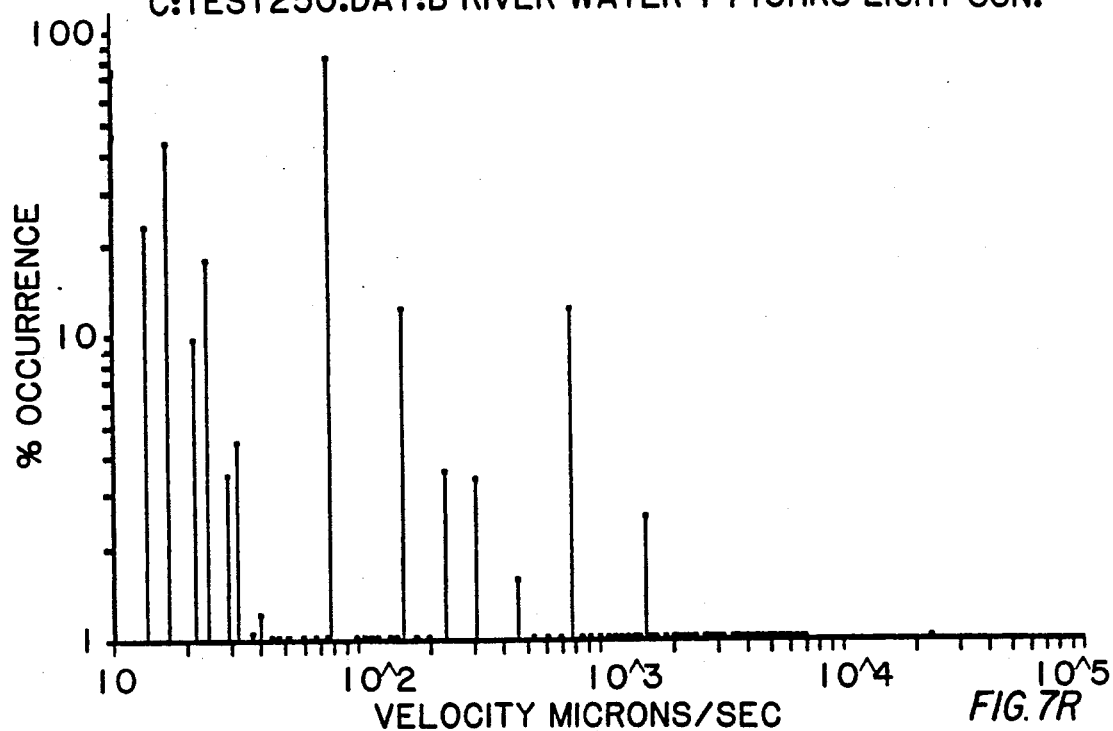
Figure 7S:
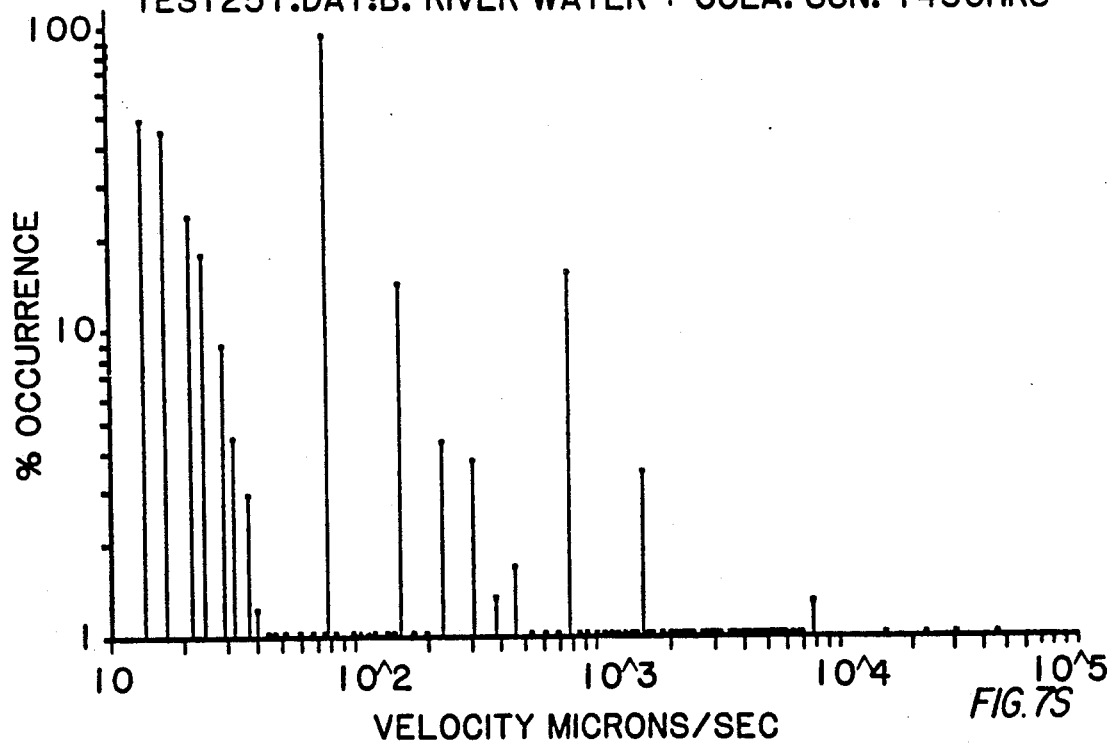

FIGS. 7i to 7p and FIGS. 7r to 7z are histograms of the Broadkill river water. In FIG. 7i not the times and relative peak heights and number of peaks. At higher resolutions the ordinate would be a forest of peaks. The number showing reflect the byte size and comprise between speed and resolution. Each plot or histogram is constructed from about 12,000 doppler measurements and took about 5 minutes to run. A date and time are set forth in the legends at the top of each figure. Note the activity variation (diurnal rhythms) culminating in a very quiet spectrum in the late evening (FIG. 7n). Up to FIG. 7o all previous measurements had been in the dark, and while FIG. 7o shows more activity, FIGS. 7p and 7r are in sunlight and show a dramatic increase in activity. FIG. 7s reflects a simple ecology experiment. In this case coca-cola (1% was added) to the sample solution and the figure illustrates the dramatic increase in activity of microbiota in the river water. Note that about 17 minutes later (FIG. 7t) activity has dramatically decreased. This indicates a sick specimen, much quieter (e.g. less active) than early morning or late evening (FIG. 7n). FIGS. 7u–7z illustrate recovery of the specimen.

In order to identify individual species, the velocity spectra of various microbiota are stored under various conditions of 1) no exogenous stimuli, 2) one selected exogenous stimuli, and 3) a plurality of selected exogenous stimuli simultaneously applied or in a given sequence. Preferably the velocity spectra are obtained at predetermined times in the natural rhythm circadian cycle of the microbiota. These tests establish the "finger print" for the individual microbiota. The velocity spectra of various selected microbiota under various exogenous stimuli are shown in FIGS. 6a–6l and it is possible to correlate the response of an unknown species to the recorded spectra in essentially the same way as finger prints identify an unknown (certain microbiota have the "swimming" patterns shown in FIG. 1(a–c) and others have "swimming" patterns shown in FIGS. 2a and 2b and with the very fine discriminations available according to the present invention, the pattern can be detected as an categorization or identification feature. The response to various exogenous stimuli is detected as a further categorization of the unknown species and so on to arrive at the correct identify of the specimen.

The invention can be used for in situ particle characterization (sizing, motion, direction) or for cataloging the feeding behavior of filter feeders. While the invention is particularly useful for stationary fluid mediums, under certain circumstances movement of the medium in a plane transverse to the vector reported by the laser dropper can increase the sampling rate. Alternately, a movement at a known rate may be compensated for by data processing.

It is believed that the system disclosed herein is so sensitive that it can detect the influence on motility of a culture due to psychodynamic energy transmitted as a stimulus to microbiota free to move in an established zone, and it is possible to serve as a communications system.

FIG. 4 discloses a further feature of the invention wherein a holographic record of the microbiota is made. In this case, a mirror M is introduced, either mechanically or electrooptically. Laser beam B would normally be crossing laser beam A inside the biospectrometer cell C. It will be appreciated that, as is conventional in holograms, the reception of scattered light must be limited to that of beam A which has come from the microbiota in the volume or sample cell. It will also be appreciated that the recording medium must be changed between exposures.

While the invention has been described in connection with a preferred embodiment thereof, it will be appreciated that various changes and modifications can be made without departing form the spirit and scope of the invention as defined in the appended claims.

What is claimed is:

1. A method of obtaining data on live microbiota, comprising,
   a) making a record of the natural rhythm circadian cycle of said live microbiota,
   b) at selected points in said rhythm circadian cycle subjecting said microbiota to a predetermined exogenous stimuli, and
   c) recording any change in the physical movements of the body and portions thereof of said microbiota, during application of said stimuli, by laser light scattering.

2. The method defined in claim 1 wherein said laser light scattering uses a pair of laser light beams, one of which has been shifted a predetermined frequency related to the body movements of the microbiota.

3. A method of measuring movement of a live microbiota in a fluid medium comprising:
   allowing said live microbiota to move in said fluid medium of its own volition, directing at least a part of laser energy beams of the same predetermined frequency along separate paths, respectively, shifting the frequency of one of said radiant energy beams a predetermined amount relative to the other of said radiant energy beams, projecting a first of said radiant energy beams through said fluid medium at a predetermined zone, projecting a second beam of said pair of radiant energy beams through said fluid medium and said predetermined zone and at a predetermined angle relative to said first beam of radiant energy, periodically applying exogenous stimuli to said microbiota, controlling the periodic application of an exogenous stimuli at selected points in the natural rhythm circadian cycle of said microbiota from one or more exogenous stimuli selected from the group consisting of:
a) a magnetic field,
b) an electric field,
c) complex electromagnetic fields including fields produced by a spark discharge,
d) variable intensity/wavelength light in the visible spectrum,
e) x-rays,
f) ultraviolet light,
g) infrared light,
h) chemical stimuli,
i) pressure,
j) sonic,
k) radio frequency, and
l) thermal;

transducing the radiant energy scattered from said predetermined zone to electronic data signals characteristic of the velocity and direction of movement of various movements of said live microbiota in said fluid medium.

4. The method defined in claim 3 including providing a microprocessor and controlling the periodic application of one or more of said exogenous stimuli by said microprocessor.

5. The method of measuring movement of live microbiota as defined in claim 3 including providing a solid state laser as the source of said pair of radiant energy beams and providing fiber optic coupling elements to constitute said separate paths.

6. A method of monitoring a fluid medium having live microbiota therein, comprising, projecting a plurality of pairs of laser beams along separate paths, each beam of a pair having the same frequency, optically shifting the frequency of one beam of each of said plurality of pairs of laser beams a predetermined amount relative to the other laser beam of a pair, converging all of said beams to a measuring volume of said fluid medium common to all said laser beams, and detecting of changes in movement of the of various movements associated with said microbiota in said medium by transducing the radiant energy scattered from said measuring volume by each of said pair of beams to electronic signals, respectively.

7. A method of measuring pollution using live microbiota, comprising,
a) allowing said live microbiota to move in a fluid medium subject to pollution,
b) subjecting said live microbiota to a pair of converged laser beams, and detecting movements thereof by laser light scattering,
c) applying a pollution stimulus to said live microbiota, and
d) detecting any change in the physical movements of the body and portions thereof of said live microbiota during application of said stimuli by laser light scattering.

8. A method of identifying an unknown microbiota species in a sample comprising:
A. establishing a library of velocity spectra for a plurality of known microbiota species by
1) monitoring the velocity spectra of said known microbiota species, with and without one or more selected exogenous predetermined stimuli applied by a laser droppler,
2) recording each monitored velocity spectra to form said library of velocity spectra,
B. monitoring the velocity spectra of said unknown microbiota species with a laser dropper and in a sample under the same conditions of selected predetermined exogenous stimuli used to form said library,
C. comparing the resulting velocity spectra of said unknown microbiota species with said library of velocity spectra to correlate the velocity spectra features and identify said unknown microbiota species.

9. The method of identifying an unknown microbiota in a sample as defined in claim 8 wherein step A.1) is performed at selected times in the natural rhythm circadian cycle of each microbiota species.

* * * * *